United States Patent
Lyerly et al.

(10) Patent No.: US 11,253,580 B2
(45) Date of Patent: Feb. 22, 2022

(54) CANCER VACCINES AND METHODS OF DELIVERY

(71) Applicant: DUKE UNIVERSITY, Durham, NC (US)

(72) Inventors: Herbert K. Lyerly, Durham, NC (US); Takuya Osada, Durham, NC (US); Zachary C. Hartman, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 112 days.

(21) Appl. No.: 16/068,587

(22) PCT Filed: Jan. 9, 2017

(86) PCT No.: PCT/US2017/012703
§ 371 (c)(1),
(2) Date: Jul. 6, 2018

(87) PCT Pub. No.: WO2017/120576
PCT Pub. Date: Jul. 13, 2017

(65) Prior Publication Data
US 2019/0022204 A1 Jan. 24, 2019

Related U.S. Application Data

(60) Provisional application No. 62/275,952, filed on Jan. 7, 2016.

(51) Int. Cl.
| | | |
|---|---|---|
| *A61K 39/00* | (2006.01) | |
| *C07K 16/32* | (2006.01) | |
| *A61P 35/00* | (2006.01) | |
| *A61K 45/06* | (2006.01) | |

(52) U.S. Cl.
CPC .. *A61K 39/001106* (2018.08); *A61K 39/0011* (2013.01); *A61P 35/00* (2018.01); *C07K 16/32* (2013.01); *A61K 45/06* (2013.01); *A61K 2039/5158* (2013.01); *A61K 2039/53* (2013.01); *A61K 2039/545* (2013.01); *A61K 2039/55522* (2013.01); *A61K 2300/00* (2013.01)

(58) Field of Classification Search
CPC combination set(s) only.
See application file for complete search history.

(56) References Cited

U.S. PATENT DOCUMENTS

| | | |
|---|---|---|
| 6,734,172 B2 | 5/2004 | Scholler et al. |
| 8,445,268 B2 | 5/2013 | Lee et al. |
| 8,846,080 B2 | 9/2014 | Biemans et al. |
| 9,216,229 B2 | 12/2015 | Brown et al. |
| 9,226,959 B2 | 1/2016 | Kramps et al. |
| 9,956,276 B2 * | 5/2018 | Lyerly ............... A61P 37/04 |
| 10,258,676 B2 * | 4/2019 | Zeng ............... A61K 39/12 |
| 2003/0143568 A1 | 7/2003 | Singer et al. |
| 2003/0228606 A1 | 12/2003 | Tatarewicz et al. |
| 2003/0232350 A1 | 12/2003 | Afar et al. |
| 2004/0253606 A1 | 12/2004 | Aziz et al. |
| 2005/0266409 A1 | 12/2005 | Brown et al. |
| 2008/0057064 A1 | 3/2008 | Zhou |
| 2009/0214518 A1 | 8/2009 | Buckanovich et al. |
| 2010/0055093 A1 | 3/2010 | Shepard et al. |
| 2010/0279399 A1 | 11/2010 | Robins et al. |
| 2011/0281748 A1 | 11/2011 | Singh et al. |
| 2012/0014984 A1 | 1/2012 | Shahabi |
| 2014/0017259 A1 | 1/2014 | Aurisicchio et al. |
| 2014/0221329 A1 | 8/2014 | Cronin et al. |
| 2014/0377261 A1 | 12/2014 | Lyerly et al. |
| 2015/0047065 A1 | 2/2015 | Brack et al. |
| 2015/0258099 A1 | 9/2015 | Hager et al. |
| 2018/0092989 A1 | 4/2018 | Lyerly et al. |
| 2018/0094050 A1 | 4/2018 | Lyerly et al. |
| 2018/0282736 A1 | 10/2018 | Lyerly et al. |

FOREIGN PATENT DOCUMENTS

| | | | |
|---|---|---|---|
| WO | WO 2003/080835 | | 10/2003 |
| WO | WO 2011/060260 | | 5/2011 |
| WO | WO 2011/146568 | | 11/2011 |
| WO | WO 2011/154863 | | 12/2011 |
| WO | WO 2012/125864 | | 9/2012 |
| WO | WO 2013/056178 | | 4/2013 |
| WO | WO 2013/110030 | * | 7/2013 |
| WO | WO 2016/007499 | | 1/2016 |
| WO | WO 2016/007504 | | 1/2016 |
| WO | WO 2017/120576 | | 7/2017 |

OTHER PUBLICATIONS

Anderson et al (Vaccine, 2007, 25S:B24-B34).*
Wang et al (Breast Cancer Research, 2007, 7:R580-R588).*
Dietz et al (Mol. Ther. 2013, 21:1526-1535).*
Clay et al (Immuno. Research, 2011, 49:235-247).*
Kleponis et al (Cancer Biology Medicine, 2015, 12:201-208).*
Skinner, Nicole Elizabeth. (2013). Dissertation. Strategies to improve gene expression and targeting for DNA vaccine development. Retrieved from the University of Minnesota Digital Conservancy, https://hdl.handle.net/11299/161088.*
Morse, MA et al. Synergism from combined immunologic and pharmacologic inhibition of HER2 in vivo. (2010) Int J Cancer 126:2893-903.
Nabholtz, J.M. et al., "Anastrozole is superior to tamoxifen as first-line therapy for advanced breast cancer in postmenopausal women: results of a North American multicenter randomized trial. Arimidex Study Group" (2000) J Clin Oncol 18(22): 3758-3767.
Nanda R, Chow LQ, Dees EC, Berger R, Gupta S, Geva R, et al. Pembrolizumab in Patients With Advanced Triple-Negative Breast Cancer: Phase Ib Keynote-012 Study. J Clin Oncol. 2016;34(21):2460-7.

(Continued)

*Primary Examiner* — Laura B Goddard
(74) *Attorney, Agent, or Firm* — Quarles & Brady LLP

(57) ABSTRACT

Disclosed are compositions, methods, and kits for treating a cancer or pre-cancer. In particular, the invention generally relates to cancer vaccines as well as methods of delivering the vaccines. Combination treatments including the vaccines in combination with immunomodulatory agents are also contemplated.

7 Claims, 15 Drawing Sheets

Specification includes a Sequence Listing.

(56) References Cited

OTHER PUBLICATIONS

O'Neil, LA et al. "Therapeutic targeting of toll-like receptors for infectious and inflammatory diseases and cnacer." (2009) Pharmacol Rev 61:177-97.
Osada, T et al. "Vaccination targeting human HER3 alters the phenotype of infiltrating T cells and respones to immune checkpoint inhibition." (2017). OncoImmunology 0(0).
Osada T, Yang XY, Hartman ZC, Glass O, Hodges BL, Niedzwiecki D, et al. Optimization of vaccine responses with an E1, E2b and E3-deleted Ad5 vector circumvents pre-existing anti-vector immunity. Cancer Gene Ther. 2009;16(9):673-82.
Pederson, MW et al. "Sym004: a novel synergistic anti-epidermal growth factor receptor antibody mixture with superior anticancer efficacy." (2010) Cancer Res 70:588-97.
Pulaski, BA et al. "Reduction of established spontaneous mammary carcinoma metastases following immunotherapy with major histocompatibility complex class II and B7.1 cell-based tumor vaccines." (1998) Cancer Res. 58:1486-93.
Renard, V. et al., "HER-2 DNA and Protein Vaccines Containing Potent Th Cell Epitopes Induce Distinct Protective and Therapeutic Antitumor Responses in HER-2 Transgenic Mice" (2003) J Immunol 171(3): 1588-1595.
Ren et al. "Polyclonal Her2-specific antibodies induced by vaccination mediate receptor internalization and degradation in tumor cells" (2012) Breast cancer research 14: R89.
Rosenberg, SA et al., Adoptive cell transfer: a clinical path to effective cancer immunotherapy. Nat. Rev. Cancer 8 (4): 299-308 (2008).
Sakai K, Yokote H, Murakami-Murofushi K, Tamura T, Saijo N, Nishio K. Pertuzumab, a novel HER dimerization inhibitor, inhibits the growth of human lung cancer cells mediated by the HER3 signaling pathway. Cancer Sci. 2007;98(9):1498-503.
Schoeberl, Birgit et al. "An ErbB3 Antibody, MM-121, Is Active in Cancers with Ligand-Dependent Activation" (2010) Cancer Research: 70(6): 2485-2494.
Soares KC, Rucki AA, Wu AA, Olino K, Xiao Q, Chai Y, et al. PD-1/PD-L1 blockade together with vaccine therapy facilitates effector T-cell infiltration into pancreatic tumors. J Immunother. 2015;38(1):1-11.
Tanaka, T. et al., "Efficient generation of antibodies to oncoproteins by using synthetic peptide antigens," (1985) Proc. Natl. Acad. Sci. USA 82:3400-3404.
Tiriveedhi V, Tucker N, Herndon J, Li L, Sturmoski M, Ellis M, Ma C, Naughton M, Lockhart AC, Gao F, et al. Safety and preliminary evidence of biologic efficacy of a mammaglobin-a DNA vaccine in patients with stable metastatic breast cancer. Clinical cancer research : an official journal of the American Association for Cancer Research. 2014;20(23):5964-75.
Topalian SL, Drake CG, Pardoll DM. Immune checkpoint blockade: a common denominator approach to cancer therapy. Cancer Cell. 2015;27(4):450-61.
Van Elsas A, Hurwitz AA, Allison JP. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. 1999;190(3):355-66.
Yoo, J.Y. et al., "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.
Yuan, J. et al., "CTLA-4 blockade increases antigen-specific CD8(+) T cells in prevaccinated patients with melanoma: three cases" (2011) Cancer Immunol Immunother, 60(8): 1137-1146.
Yu, P et al. "Targeting the primary tumor to generate CTL for the effective eradication of spontaneous metastases." (2007) J Immunol 179:1960-8.
Zitvogel, L et al. "The anticancer immune response: indispensable for therapeutic success?" (2008) 118:1991-2001.

International Search Report and Written Opinion for PCT/US2017/012703 dated Apr. 3, 2017 (18 pages).
Emens LA, Braiteh FS, Cassier P, DeLord J-P, Eder JP, Shen X, et al. Abstract PD1-6: Inhibition of PD-L1 by MPDL3280A leads to clinical activity in patients with metastatic triple-negative breast cancer. Cancer Res. 2015;75(9 Supplement):PD1-6-PD1-6.
Liddy et al., Monoclonal TCR-redirected tumor cell killing. Nature Med. 18:980-7 (2012).
Roskoski R, Jr. The ErbB/HER family of protein-tyrosine kinases and cancer. Pharmacological research : the official journal of the Italian Pharmacological Society. 2014;79:34-74.
Shin DS, Ribas A. The evolution of checkpoint blockade as a cancer therapy: what's here, what's next? Curr Opin Immunol. 2015;33:23-35.
Agus, DB et al. "Targeting ligand-activated ErbB2 signaling inhibits breast and prostate tumor growth." (2002) 2:127-37.
Amalfitano A, Hauser MA, Hu H, Serra D, Begy CR, Chamberlain JS. Production and characterization of improved adenovirus vectors with the E1, E2b, and E3 genes deleted. J Virol. 1998;72(2):926-33.
Amin, DN et al. "The role of HER3, the unpretentious emmber of the HER family, in cancer biology and cancer therapuetics." (2010) Semin Cell Dev Biol 2010:8.
Arteaga et al.. Treatment of HER2-positive breast cancer: current status and future perspectives. Nature Reviews Clinical Oncology, 9: 16-32, 2012.
Atkins, MB et al. "Phase I evaluation of intravenous recombinant human interleukin 12 in patients with advanced malignancies." (1997) Clin Cancer Res 3:409-17.
Ben-Kasus, T. et al. "Persistent elimination of ErbB-2/HER2-overexpressing tumors using combinations of monoclonal antibodies: relevance of receptor endocytosis." (2009) Proc Natl Acad Sci USA 106:3294-99.
Binder DC, Engels B, Arina A, Yu P, Slauch JM, Fu YX, et al. Antigen-specific bacterial vaccine combined with anti-PD-L1 rescues dysfunctional endogenous T cells to reject long-established cancer. Cancer immunology research. 2013;1(2):123-33.
Blattman, JN et al. "Cancerimmunotherapy: a treatment for the masses." (2004) Science 305:200-5.
Cai Z, Zhang H, Liu J, Berezov A, Murali R, Wang Q, et al. Targeting erbB receptors. Seminars in cell & developmental biology. 2010;21(9):961-6.
Campbell, MR et al. "HER3 comes of age: new insights into its functions and role in signaling, tumor biology, and cancer therapy." Clin cancer Res (2010) 16:1373-83.
Castiglioni et al. Role of exon-16-deleted HER2 in breast carcinomas. (2006) Endocr Relat Cancer: 13(1): 221-232.
Castagnoli, L. et al., "Activated d16HER2 homodimers and SRC kinase mediate optimal efficacy for trastuzumab" (2014) Cancer Res 74(21): 6248-6259.
Clay, T. et al., "Polyclonal Immune Responses To Antigens Associated With Cancer Signaling Pathways And New Strategies To Enhance Cancer Vaccines" (2011) Immunolo Res 49(0): 235-247.
Drake, CG et al. Mechanisms of immune evasion by tumors. (2006) Adv Immunol 90:51-81.
Dranoff, G. "Cytokines in cancer pathogenesis and cancer therapy." (2004) Nat Rev Cancer 4:11-22.
Eager, R et al. "GM-CSFF gene-transduced tumor vaccines." (2005) Mol Ther. 12:18-27.
Fourcade J, Sun Z, Pagliano O, Chauvin JM, Sander C, Janjic B, et al. PD-1 and Tim-3 regulate the expansion of tumor antigen-specific CD8(+) T cells induced by melanoma vaccines. Cancer Res. 2014;74(4):1045-55.
Friedman, LM et al. "Synergistic down-regulation of receptor tyrosine kinase by combinations of mAbs: implications for cancer immunotherapy." (2005) Proc Natl Acad Sci USA 102:1915-20.
Fu, J. et al., "Preclinical evidence that PD1 blockade cooperates with cancer vaccine TEGVAX to elicit regression of established tumors" (2014) Cancer Res, 74(15): 4042-4052.
Gala K, Chandarlapaty S. Molecular pathways: HER3 targeted therapy. Clin Cancer Res. 2014;20(6):1410-6.
Gallo, P. et al., "Xenogenic Immunization in Mice Using HER2 DNA Delivered by an Adenoviral Vector" (2005) Int. J. Cancer 113(1): 67-77.

(56) References Cited

OTHER PUBLICATIONS

Giltnane JM, Moeder CB, Camp RL, Rimm DL. Quantitative multiplexed analysis of ErbB family coexpression for primary breast cancer prognosis in a large retrospective cohort. Cancer. 2009;115(11):2400-9.
Goldman, B et al. "The cancer vaccine roller coaster." (2009) Nat Biotechnol 27:129-39.
Greenspan, N.S. et al., "Defining epitopes: It's not as easy as it seems," (1999) Nature Biotechnology 7:936-937.
Grupp et al., Chimeric antigen receptor-modified T cells for acute lymphoid leukemia. New England J. Med. 368:1509-18, (2013).
Hartman, Z. et al., "An Adenoviral vaccine encoding full-length inactivated human Her2 exhibits potent immunogenicity and enhanced therapeutic efficacy without oncogenicity" (2010) Clin Cancer Res 16(5): 1466-1477.
Hartman, Z. et al., "Ligand-independent TLR signals generated by ectopic overexpression of MyD88 generate local and systemic anti-tumor immunity" (2010) Cancer Res 70(18): 7209-7220.
Hartman, Z. et al., "Growth of triple-negative breast cancer cells relies upon coordinate autocrine expression of the proinflammatory cytokines IL-6 and IL-8" (2013) Cancer Res 73(11): 3470-3480.
Hartman, Z. et al., Increasing vaccine potency through exosome antigen targeting. Vaccine. Nov. 21, 2011;29(50):9361-7.
He, TC et al. "A simplified system for generating recombinant adenoviruses." (1998) Proc Natl Acad Sci USA 95:2509-14.
Hodges, BL et al. "Adenovirus vectors with the 100K gene deleted and their potential for multiple gene therapy applications." (2001) J Virol 75:5913-20.
Hsieh AC, Moasser MM. Targeting HER proteins in cancer therapy and the role of the non-target HER3. Br J Cancer. 2007;97(4):453-7.
Ignatiadis, M. & Sotiriou, C. "Luminal breast cancer: from biology to treatment" (2013) Nature Rev Clin Oncol 10, 494-506.
Karyampudi L, Lamichhane P, Scheid AD, Kalli KR, Shreeder B, Krempski JW, et al. Accumulation of memory precursor CD8 T cells in regressing tumors following combination therapy with vaccine and anti-PD-1 antibody. Cancer Res. 2014;74(11):2974-85.
Kennecke, H. et al., "Metastatic behavior of breast cancer subtypes" (2010) J Oncol 28(20): 3271-3277.
Kershaw, M.H. et al., "Gene-engineered T cells as a superior adjuvant therapy for metastatic cancer" (2004) J Immunol 173(3): 2143-2150.
Kol A, Terwisscha van Scheltinga AG, Timmer-Bosscha H, Lamberts LE, Bensch F, de Vries EG, et al. HER3, serious partner in crime: therapeutic approaches and potential biomarkers for effect of HER3-targeting. Pharmacol Ther. 2014;143(1):1-11.
Laheru, DA eta l. "Genes to vaccines for immunotherapy: how the molecular biology revolution has influenced cancer immunology." (2005) Mol Cancer Ther 4:1645-52.
Lee CH, Huntsman DG, Cheang MC, Parker RL, Brown L, Hoskins P, et al. Assessment of Her-1, Her-2, And Her-3 expression and Her-2 amplification in advanced stage ovarian carcinoma. Int J Gynecol Pathol. 2005;24(2):147-52.
Lee-Hoeflich, ST et al. "A central role for HER3 in HER2-amplified breast cancer: implications for targeted therapy." (2008) Cancer Res 68:5878-87.
Leonard, JP et al. "Effects of single-dose interleukin-12 exposure on interleukin-12-associated toxicity and interferon-y production." (1997) Blood 90:2541-8.
Li B, VanRoey M, Wang C, Chen TH, Korman A, Jooss K. Anti-programmed death-1 synergizes with granulocyte macrophage colony-stimulating factor-secreting tumor cell immunotherapy providing therapeutic benefit to mice with established tumors. Clin Cancer Res. 2009;15(5):1623-34.
Luo, et al. "A protocol for rapid generation of recombinant adenoviruses using the AdEasy system" (2007) Nature Protocols 2:1236.
Makhija, S et al. "clinical activity of gemcitabine plus pertuzumab in platinum-resistant ovarian cancer, fallopian tube cancer, or primary peritoneal cancer." (2010) J Clin Oncol 28:1215-23.
Mitra, D. "An oncogenic isoform of HER2 associated with locally disseminated breast cancer and trastuzumab resistance" (2009) Mol Cancer Ther 8(8): 2152-2162.
Chabot, S. et al., "Minicircle DNA electrotransfer for efficient tissue-targeted gene delivery," Gene Therapy (2013) 20:62-68.
Kako, K. et al., "Effects of inflammatory response on In Vivo transgene expression by plasmid DNA in mice," Journal of Pharmaceutical Sciences (2008) 97(8):3074-3083.
Kaufman, H. L. et al., "Phase II Randomized Study of Vaccine Treatment of Advanced Prostate Cancer (E7897): A Trial of the Eastern Cooperative Oncology Group," J. Clin. Oncol. (2004) 22:2122-2132.
Munye, M. M. et al., "Minicircle DNA Provides Enhanced and Prolonged Transgene Expression Following Airway Gene Transfer," Scientific Reports (2016) 6:23125 | DOI: 10.1038/srep23125.
Yew, N.S. et al., "Reduced Inflammatory Response to Plasmid DNA Vectors by Elimination and Inhibition of Immunostimulatory CpG Motifs," Molecular Therapy (2000) 1(3):255-262.

\* cited by examiner

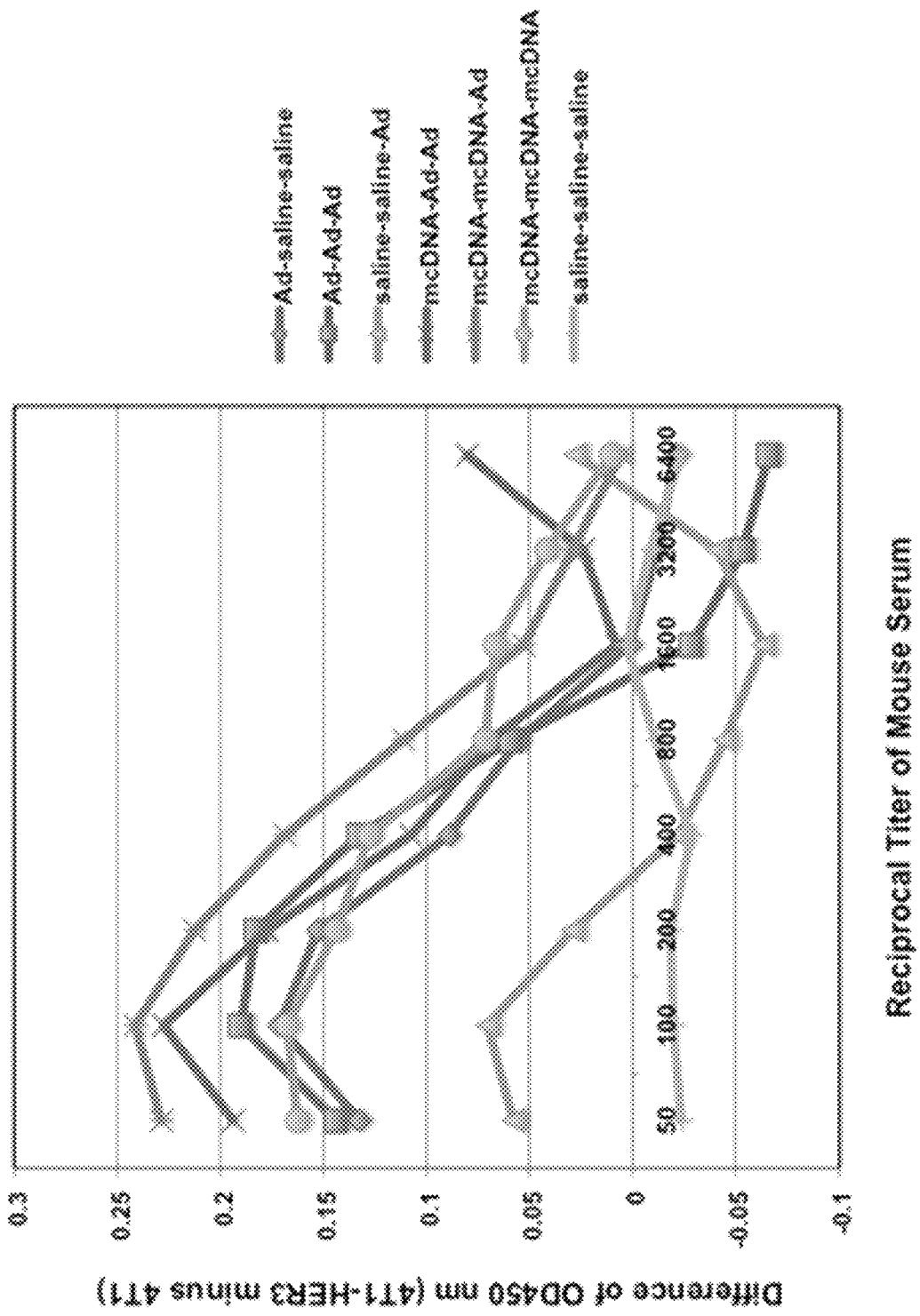

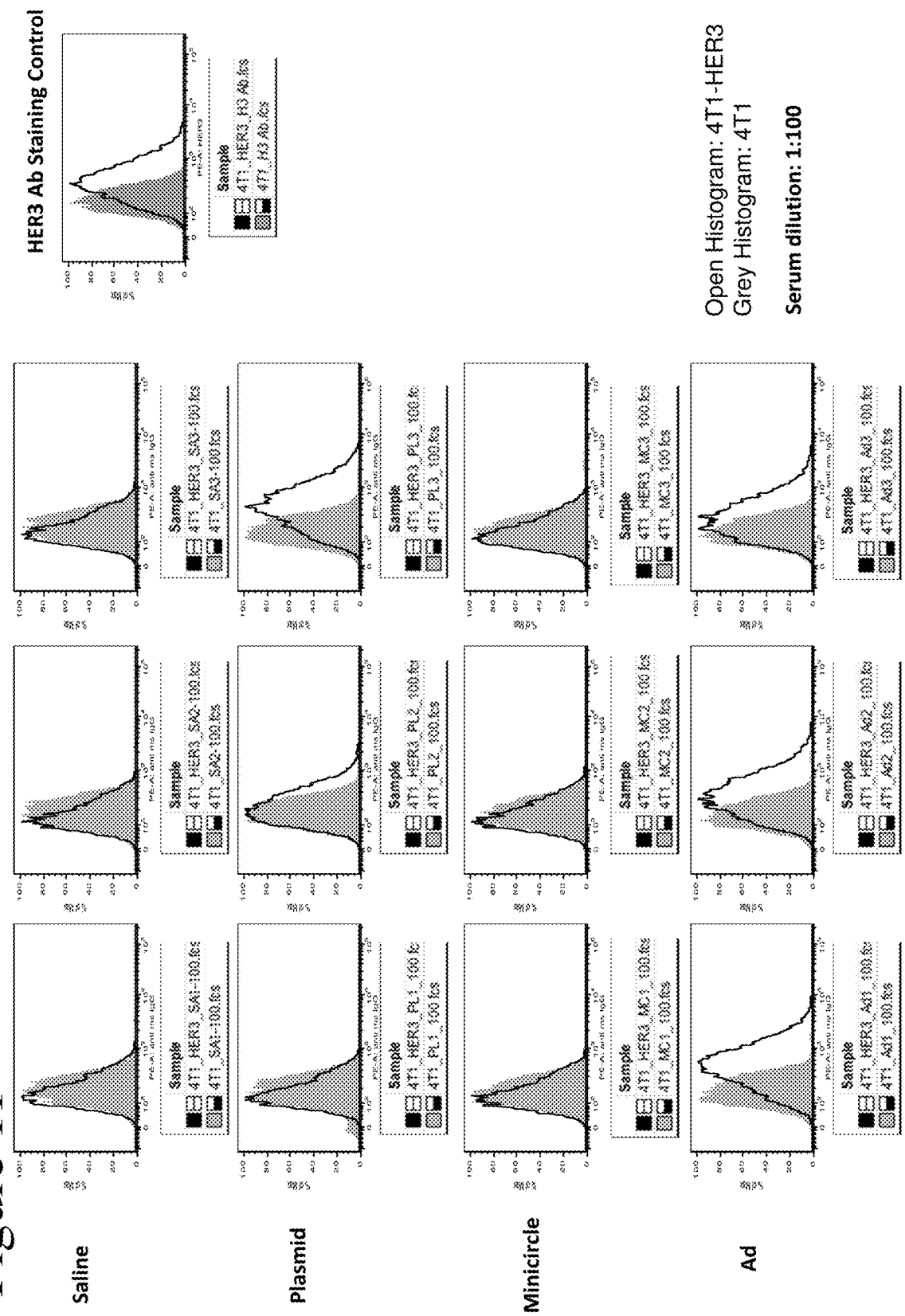
Figure 11

CANCER VACCINES AND METHODS OF DELIVERY

CROSS-REFERENCE TO RELATED PATENT APPLICATIONS

The present application is a national stage filing under 35 U.S.C. 371 of International Application No. PCT/US2017/012703, filed Jan. 9, 2017, which claims the benefit of priority to U.S. Provisional Patent Application No. 62/275,952, filed on Jan. 7, 2016, both of which are incorporated herein by reference in their entirety.

STATEMENT REGARDING FEDERALLY SPONSORED RESEARCH

This invention was made with United States government support awarded by the Department of Defense grant number BC113107. The United States has certain rights in this invention.

SEQUENCE LISTING

This application is being filed electronically via EFS-Web and includes an electronically submitted Sequence Listing in .txt format. The .txt file contains a sequence listing entitled "2017-01-09_5667-00376_ST25_Sequence_Listing.txt" created on Jan. 9, 2017 and is 151,883 bytes in size. The Sequence Listing contained in this .txt file is part of the specification and is hereby incorporated by reference herein in its entirety.

INTRODUCTION

Cancer vaccines target antigens expressed by tumors, but application of these vaccines has not been as effective as once hoped due to induction of immune tolerance by chronic overexpression of the targeted protein in the absence of co-stimulatory molecules and the induction of an immunomodulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with what antigens and using what vaccination strategies. In contrast, a strategy is proposed here in which vaccination against the antigen(s) that will predictably be overexpressed in response to a therapy, but prior to that antigen's over-expression by the cancer cells is used to induce a robust anti-cancer immune response.

This application generally relates to cancer vaccines and methods of delivery. More specifically, the vaccines may be directed against antigens such as HER2, HER3, and ESR1 isoforms that are expressed on cancer cells or in response to development of resistance to a therapeutic intervention to cancer (or pre-cancers). Methods of delivering the vaccines and combination treatments including the vaccines in combination with immunomodulatory agents are also provided.

SUMMARY

In one aspect, polynucleotide constructs including a heterologous promoter operably connected to a first polynucleotide encoding a first antigenic polypeptide are provided. The polynucleotide constructs may be circular and/or may lack a bacterial origin of replication and/or an antibiotic resistance gene.

In a further aspect, methods of treating a cancer or pre-cancer or of reducing the likelihood of the cancer developing resistance to a cancer therapeutic or prevention agent in a subject are provided. The methods may include administering to the subject a therapeutically effective amount of a DNA vaccine and administering to the subject a therapeutically effective amount of a vaccine vector composition. Preferably, the DNA vaccine includes a first polynucleotide encoding a first antigenic polypeptide and the vaccine vector composition includes a second antigenic polypeptide.

In a still further aspect, cancer vaccine kits are provided. The cancer vaccine kits may include a DNA vaccine component including a first polynucleotide encoding a first antigenic polypeptide and a vaccine vector component including a second antigenic polypeptide. Suitably, the DNA vaccine component includes any one of the polynucleotide constructs described herein.

BRIEF DESCRIPTION OF THE DRAWINGS

FIG. 3A shows cell-based ELISA data. Two weeks after the final vaccination, mice were euthanized and blood was collected individually. Cell-based ELISA was performed for individual mouse serum using 4T1 cell-coated and 4T1-HER3 cell coated plates. Serum was titrated from 1:50 to 1:6400, added onto 4T1 or 4T1-HER3 cells and incubated. The differences of OD 450 values are shown.

FIG. 11 shows histogram overlays (4T1-HER3 vs. 4T1) for different vaccination strategies.

DETAILED DESCRIPTION

Figure 1:
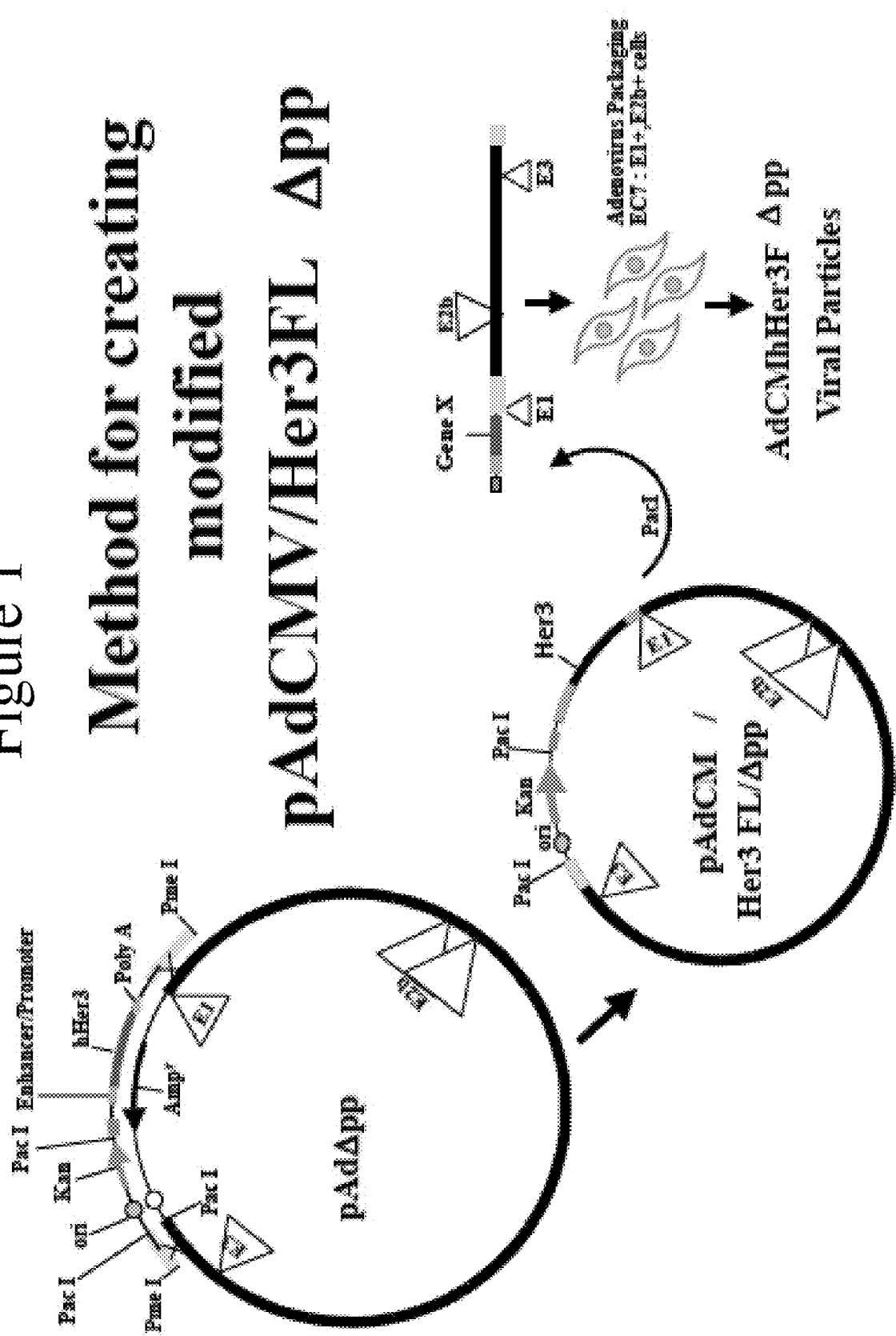
FIG. 1 shows the construction of pAdCMV/HER3/Δpp vector.

Approximately 70% of all breast cancers are classified as estrogen receptor positive (ER+); dependent upon constitutive estrogen receptor signaling. Although different classes of endocrine (anti-estrogen) therapies (including selective estrogen receptor modulators (SERMS), downregulators, and aromatase inhibitors (AIs)) are effective treatments for these cancers in adjuvant settings, approximately 50% of women will eventually relapse and die from metastatic ER+ disease. Thus, despite the advent of newer therapies (such as AIs) there remains an unrelenting rate of recurrence in ER+ breast cancer, particularly in cases where metastasis has occurred. Significantly, all patients that develop metastatic ER+ disease will progress to an endocrine therapy resistant disease. At this stage, there is no cure for ER+ breast cancer. Because compensatory mechanisms appear to account for resistance that develops in a significant percentage of anti-estrogen treated patients, we propose a novel approach that has the potential to target critical driver mutations for the lifetime of the patient. Described herein are specifically targeted immunotherapy-based vaccines and vaccine strategies directed toward specific resistance drivers that are predictably evoked by compensatory resistance mechanisms.

As a novel alternative to vaccines targeting well established tumor antigens, we hypothesized that the antigen-specific immune non-responsiveness to conventional tumor-associated antigens may be avoided by targeting tumor antigens that are induced after exposure to a cancer therapeutic or prevention agent as a mechanism of developing therapeutic resistance.

Although there may be many potential antigens overexpressed in response to a cancer therapeutic or prevention agent, those antigens that are likely critical components of specific therapeutic resistance mechanisms would be attractive targets, as immunologic ablation of clones expressing such antigens should eliminate the clinical recurrence of therapy resistant tumor cells. Antigens thought to be essential to therapeutic resistance include members of the HER family of receptor tyrosine kinases (RTKs), HER2, HER3 and also the estrogen receptor alpha (ESR1).

HER2 is a preferred dimerization partner for other HER proteins, such as HER3, with which it heterodimerizes. Dimerization with HER2 results in the autophosphorylation of tyrosine residues within the cytoplasmic domain of the receptors and initiates a variety of signaling pathways.

HER2 has tumor promoting functions in some cancers, and amplification or over-expression of HER2 is associated with increased disease recurrence and poor prognosis. Treatment of HER2-amplified breast cancers with HER2-targeting tyrosine kinase inhibitors (TKIs) leads to an increase in HER3 expression and downstream signaling that results in therapeutic resistance.

For example, the anti-HER2 monoclonal antibody pertuzumab disrupts neuregulin-induced HER2-HER3 dimerization and signaling; however, it is less effective at disrupting the elevated basal state of ligand-independent HER2-HER3 interaction and signaling in HER2-overexpressing tumor cells. Other HER3-specific antibodies under development bind to, and cause internalization of, HER3, inhibiting downstream signaling. As an alternative to monoclonal antibodies, we have recently demonstrated that polyclonal antibodies induced by vaccination against receptors such as HER2 and HER3 can mediate profound receptor internalization and degradation, providing a therapeutic effect in vitro and in vivo (Ren et al., Breast cancer Research 2012 14: R89 and International Patent Application No. WO 2013/110030, both of which are incorporated herein by reference in their entireties).

Vaccine strategies meant to target common means of therapeutic resistance by eliciting an immune response directed to at least one of HER3, HER2 or ESR1 are provided herein. The vaccine may be a vaccine vector or DNA vaccine composed of one or multiple forms of the HER2 gene deleted for exon 16 (48 bp deletion starting at nucleotide 1899 or portions thereof), a HER3 gene comprising the full-length HER3 or portions thereof or an ESR1 gene, encoding mutant forms of ESR1, such as those described in WO 2016/007504. These polynucleotides may be included in a platform, such as a DNA vaccine, or vaccine vector such as liposomal, bacterial, yeast or viral vector that would elicit an immune response to epitopes expressed from these genetic constructs. Alternatively or in addition to the genetic constructs described, polypeptides encoded by these genes or genetic constructs may be used in vaccine formulations as described below to elicit an immune response. We expect that the vaccination strategies disclosed herein which selectively target antigens related to resistance to anti-cancer therapies may block resistance development.

The vaccine vectors, DNA constructs or polypeptide based vaccine formulations described herein may include polynucleotides encoding any antigenic polypeptides or the antigenic polypeptides. The antigenic polypeptides may be selected from the group consisting of HER2d16 (SEQ ID NO: 3), Her2d16Ki (SEQ ID NO: 4), HER2d16TM (SEQ ID NO: 5), ESR1 Y537N (SEQ ID NO: 6), ESR1 Y537S (SEQ ID NO: 7), ESR1 D538G (SEQ ID NO: 8), ESR1 K303R (SEQ ID NO: 9), HER3 (SEQ ID NO: 1), HER3 (SEQ ID NO: 2), and HER3 epitopes (SEQ ID NOs: 13-30) or portions or combinations thereof. The portion of HER2d16 included in the vaccine should include the junction of the deletion in exon 16 in various isoforms. The deletion of exon 16 begins at amino acid 633 in the amino acid sequence of SEQ ID NO: 3. Those of skill in the art would expect the epitopes to be 6, 8, 10, 12, 14, 16, 18 or 20 amino acids in length. Thus the portions referred to should be at least long enough to contain an epitope. The vaccines used in the Examples encompass larger polypeptides, but vaccines may include smaller portions of the polypeptides than those provided herein. The vaccines may include the region flanking the deletion at amino acid 633 of SEQ ID NO: 3 or the region flanking the mutations at positions 537, 538 or 303 of ESR1. The vaccines and vaccine formulation may include a polynucleotide encoding a polypeptide or a polypeptide at least 8, 10, 12, 14, 16, 18, 20 or more amino acids in length.

The polynucleotide encoding HER2d16, ESR1 or HER3 polypeptides may be encompassed in a vaccine vector. For example, SEQ ID NOs: 31-33 (nucleic acid sequences of the HER2d16) or portions thereof may be comprised in a vaccine. Suitable vaccine vectors include, but are not limited to viral vectors such as adenoviral, fowlpox, vaccinia, VEE, etc., DNA-based vaccination vectors. Vaccine formulations using protein/peptide vaccination strategies may also be used and for example may include formulations including SEQ ID NO: 3, 4, and/or 5. Liposomes, yeast or bacterial vaccine vectors may also be suitable. This immunotherapeutic platform could be used prior to the development or identification of cancer types dependent upon HER2-mediated signaling, prior to the development of endocrine resistance, may be used in front line or adjuvant settings as a treatment for these cancers, and also as a preventive measure to prohibit the development and evolution of this signaling pathway as a resistance pathway.

The vaccines or vaccine vectors may include polynucleotides encoding additional polypeptides, such as other identified HER2, HER3, ESR1 polypeptides or other polypeptides comprising mutations such as those provided in SEQ ID NOs: 34-39, SEQ ID NOs: 40-44, or any of the epitopes provided in International Publication No. WO2013/110030, which is incorporated herein by reference in its entirety. The vaccine vectors including polynucleotides encoding polypeptides may also include a promoter operably connected to the polynucleotide such that the polynucleotide is capable of being expressed by the vaccine vector. The promoter may be a heterologous promoter. Those skilled in the art are capable of choosing an appropriate promoter and many are known in the art. The vaccines or vaccine vectors may also include or be administered in conjunction with a checkpoint inhibitory immunomodulatory agent. The checkpoint inhibitory immunomodulatory agent may be an antibody antagonistic for an inhibitory checkpoint molecule selected from CTLA-4, PD1, PD-L1, A2AR, B7-H3 (CD276), B7-H4, BTLA, IDO, KIR, LAGS, TIM-3, and VISTA. A PD1 antibody may be obtained from BioXCell called RMP1-14 and a CTLA-4 antibody may be from BioXCell called 9D9. Other similar antibodies are commercially available or in clinical trials such as ipilimumab, pembrolizumab, and nivolumab.

Generation of resistance to cancer therapeutic or prevention agents is a common problem in the treatment of cancer or pre-cancer and in several cases the mechanism of resistance to the therapeutic agent is known. Resistance is often the result of changes in gene expression (over-expression or blocked expression of a protein), change in the gene by mutation, or altered sequences by altered splicing or translocation or altered activation of a protein in the cells (over-activation or blocked activation of a protein).

In those cases where over-expression or over-activation of a protein, or a new sequence in the protein is responsible for increasing the resistance of the cancer or pre-cancer cells to the therapeutic or prevention agent, we report a method for reducing the likelihood that the cancer or pre-cancer will develop resistance to the cancer therapeutic or prevention agent. As used herein, resistance to a cancer therapeutic or prevention agent indicates that the cancer therapeutic or prevention agent is not as effective at inhibiting the growth of, or killing, cancer or pre-cancer cells in response to the cancer therapeutic or prevention agent. The method may even block the development of resistance to the cancer therapeutic or prevention agent or may reverse resistance to the cancer therapeutic or prevention agent after it has developed. The methods include administering the cancer therapeutic or prevention agent and administering at least one vaccine formulation to the subject in need of treatment for a cancer. The vaccine formulations described herein comprise a polynucleotide encoding a polypeptide or a polypeptide whose expression or activation is correlated with or results in development of resistance of the cancer or pre-cancer to the cancer therapeutic or prevention agent. The vaccines provided herein include a HER2 polypeptide, HER3 polypeptide or ESR1 polypeptide or a polynucleotide encoding a HER2 polypeptide such as the HER2d16 polypeptide, HER3 polypeptide or ESR1 polypeptide.

The vaccine formulations may be administered before, during or after treatment with a cancer therapeutic or prevention agent or may be administered simultaneously with the cancer therapeutic or prevention agent. As demonstrated in the Examples, more than one vaccine formulation may be administered to the subject and the administration of the more than one vaccine formulation may occur over a period of time. The administration of the vaccine formulations and the cancer therapeutic or prevention agent to the subject reduces the likelihood that the subject's cancer or pre-cancer will develop resistance to the therapeutic or prevention agent as compared to a control subject with a similar cancer or pre-cancer not administered the vaccine formulations or as compared to the general likelihood of a population of subjects having the cancer or pre-cancer. In some embodiments, the cancer or pre-cancer in individuals administered both the vaccine formulations and the therapeutic or prevention agent does not develop resistance to the cancer therapeutic or prevention agent and is treated. Alternatively, the growth of the cancer or pre-cancer may be inhibited or the growth rate reduced. The administration of the vaccine formulations and cancer therapeutic or prevention agent may also reverse resistance to the cancer therapeutic or prevention agent if the cancer or pre-cancer is already resistant to the cancer therapeutic or prevention agent. In some embodiments, administration of the vaccine formulations is sufficient to treat the cancer or inhibit the growth or kill the cancer. In other embodiments, the vaccine formulations must be administered in conjunction with the cancer therapeutic or prevention agent or prior to development of resistance to the cancer therapeutic or prevention agent by the cancer.

The vaccine formulations may include a polynucleotide encoding a HER2, HER3 or ESR1 polypeptide or one of the listed polypeptides in a peptide-based vaccine formulation. The HER2d16 protein sequence is provided in SEQ ID NO: 3. The vaccine may comprise full-length HER2d16 or portions thereof such as shown in SEQ ID NO: 4 and SEQ ID NO: 5. For example, the vaccine may comprise only the extracellular domain or the extracellular domain plus the transmembrane domain or other portions of the HER2 polypeptide. The vaccine may include a polynucleotide encoding an ESR1 polypeptide. Three point mutations (4 mutant forms) of ESR1 associated with resistance to cancer therapeutic agents are provided as SEQ ID NOs: 6-9. The vaccine may comprise full-length ESR1 or portions thereof. For example, the vaccine may comprise only the epitopes identified in the examples of WO 2016/007504 or peptides comprising the mutations or deletions associated with resistance. The vaccine may include a polynucleotide encoding full-length HER3 polypeptide or the HER3 polypeptide itself as defined in SEQ ID NOs: 1 or 2 or portions thereof such as those defined in SEQ ID NOs: 13-30.

Suitably the vaccine is capable of eliciting an immune response to the polynucleotide or polypeptide included in the vaccine formulation in a subject administered the vaccine. The immune response may be a B cell or T cell response. Suitably the immune response includes an antibody response directed to the polypeptide included in the vaccines. The immune response may be directed to an epitope flanking or overlapping the mutation site or may be directed to a native portion of the polypeptide. The immune response may be a polyclonal antibody response in which multiple epitopes of the polypeptide are recognized by antibodies.

HER2d16 contains a deletion in exon 16 of HER2. The deletion results in a unique junction section in the peptide and epitopes spanning this junction can be generated using the vaccines described herein. Those of skill in the art will appreciate that a vaccine including polynucleotides encoding only portions of full-length HER2, i.e. antigenic epitopes, may be used in the vaccines described herein. Portions of the HER2 including the junction site at the point of deletion can be included in the vaccine. The ESR1 polypeptide sequences disclosed in SEQ ID NOs: 6-9 also contain mutations associated with therapeutic resistance. The mutations result in a unique sequence in the peptide and epitopes spanning these mutations can be identified and antibodies generated using the vaccines described herein. Those of skill in the art will appreciate that a vaccine including polynucleotides encoding only portions of full-length ESR1, i.e. antigenic epitopes, or these peptides themselves may be used in the vaccines described herein. Some potential epitopes are identified in WO 2016/007504 at Table 1 and in WO2016/007499. Portions of the HER2 or ESR1 including the mutation sites or portions of HER3 can be included in the vaccine.

The vaccine formulation may include a vaccine vector. The vaccine vector may be bacterial, yeast, viral or liposomal vaccine vector. The vaccine vector may be an adenovirus, adeno-associated virus, fowlpox, vaccinia, viral equine encephalitis virus, venezuelan equine encephalitis virus or other viral vaccine vectors. One method for generating adenovirus vectors is provided in Luo et al., Nature Protocols, (2007) 2: 1236-1247, which is incorporated herein by reference. The vaccine vector may contain the HER2, HER3 or ESR1 polynucleotide or portions thereof. The vaccine vector may contain the HER2, HER3, or ESR1 polypeptide or portions thereof. The vaccine vector may express the HER2, HER3, or ESR1 polypeptide or portions thereof. The HER2, HER3 or ESR1 polypeptide or portions thereof may be expressed on the surface or interior of the vaccine vector. The HER2, HER3 or ESR1 polynucleotide or portions thereof may be carried within the vaccine vector and the HER2, HER3 or ESR1 polypeptide or portions thereof may be expressed only after vaccination. The HER2, HER3 or ESR1 polypeptides or portions thereof may be expressed as a fusion protein or in conjunction with adjuvants or other immunostimulatory molecules to further enhance the immune response to the polypeptide.

The vaccine formulations also include DNA vaccines and peptide based vaccines as well and thus may or may not include a vaccine vector. DNA vaccines include plasmid and minicircle-based polynucleotide constructs. For example, polynucleotide constructs including a heterologous promoter operably connected to a first polynucleotide encoding a first antigenic polypeptide are provided. The polynucleotide constructs may be linear or circular in nature. As used herein, a "heterologous promoter" refers to any promoter not naturally associated with a polynucleotide to which it is operably connected. Suitable promoters include any promoters capable of expressing a polynucleotide in a eukaryotic host cell. Although the eukaryotic promoter used in the plasmid and minicircle constructs of the Examples was a CMV or EF1a promoter many other eukaryotic promoters can also be used. Other illustrative eukaryotic promoters include, but are not limited to, human gene promoters or viral promoters such as the SV40 late promoter, RSV1TK promoter, adenovirus promoter, and mouse sarcoma virus promoter.

Figure 7:
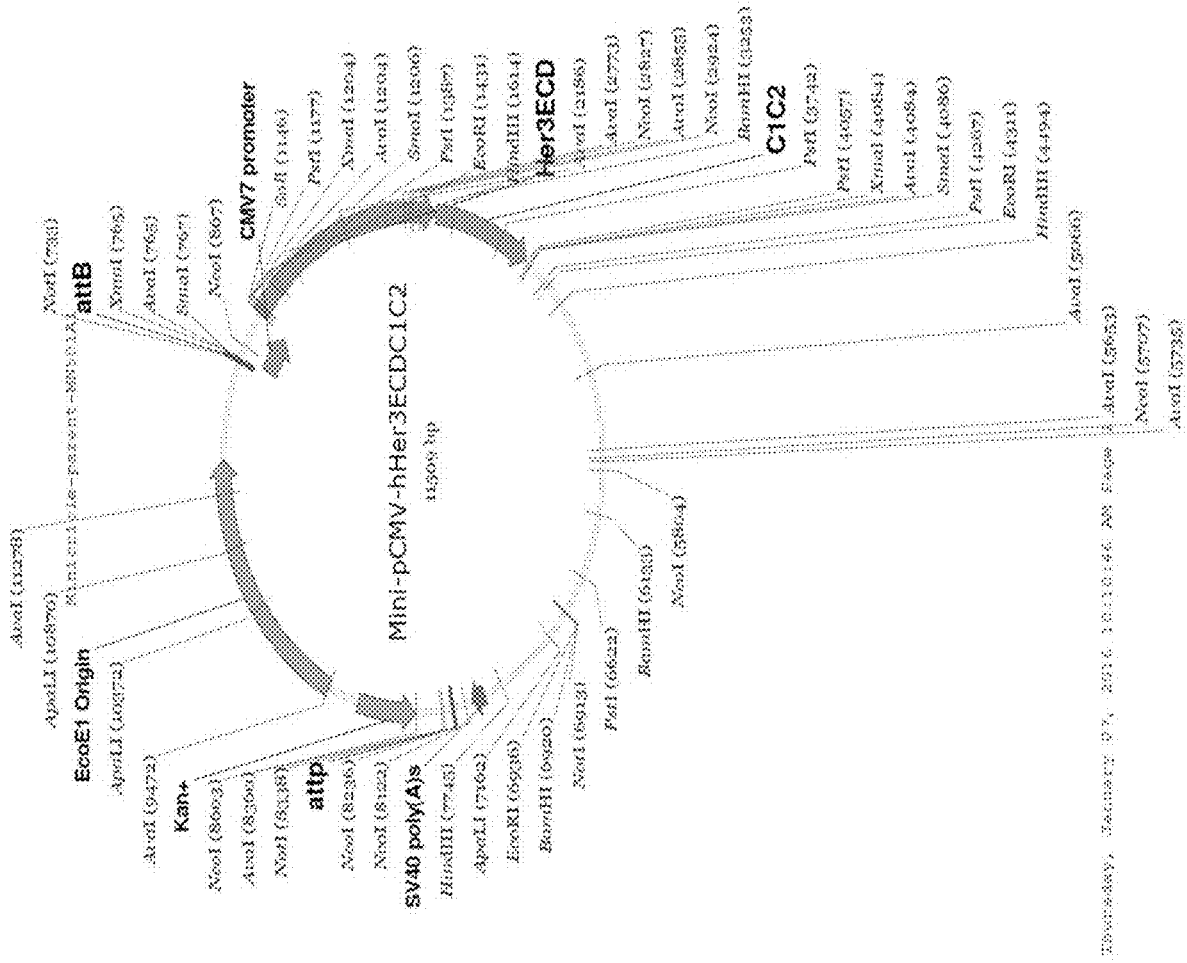
FIG. 7 is a schematic representation of the plasmid used to generate the minicircle DNA used in the Examples including the pCMV-hHER3ECD-C1C2 construct capable of generating the HER3ECD-C1C2 fusion protein.

In some embodiments, the polynucleotide constructs are circular and lack a bacterial origin of replication and an antibiotic resistance gene. For example, in the illustrative Examples, the inventors have developed minicircle constructs. The minicircle constructs are episomal DNA vectors that are produced as circular expression cassettes devoid of any bacterial plasmid DNA backbone. See, e.g. System Biosciences, Mountain View Calif., MN501A-1. Their smaller molecular size enables more efficient transfections and offers sustained expression over a period of weeks as compared to standard plasmid vectors that only work for a few days. The minicircle constructs can be derived from a plasmid with a bacterial origin of replication and optionally antibiotic resistance genes flanked by att sites to allow for recombination and exclusion of the DNA between the att sites and formation of the minicircle DNA. Such a construct is depicted in FIG. 7.

The antigenic polynucleotides and antigenic polypeptides described herein may also be linked to fusion partners such as fusion polynucleotides or polypeptides which provide additional functionality to the antigenic cargo. In some embodiments, the polynucleotide constructs described herein include a first polynucleotide that is fused in frame to a second polynucleotide encoding a lactadherin polypeptide or portions thereof. Lactadherin is a protein that is trafficked to exosomes though its C1C2 domain, a lipid binding domain. In some embodiments, the lactadherin polypeptide includes SEQ ID NO: 10 (C1C2 domains of mouse lactadherin) or a homolog thereof. In the Examples the HER3 extracellular domain was fused to lactadherin C1C2 as shown in SEQ ID NO: 11 and 12 (nucleic acid and amino acid sequences). In another embodiment the polynucleotides constructs or the encoded polypeptides may be fused with polynucleotides or their encoded polypeptides to allow delivery to and/or fusion with the cell. For example, fusion with a Herpes Simplex Virus VP16 may allow for the cellular delivery of the antigenic polypeptide. Other potential fusion protein partners are ligands for receptors found on the target cells such that the peptides will be taken up by the cells via receptor-mediated endocytosis.

Peptides may also be altered to make them more stable for delivery. Peptides may also be circularized or dimerized using any other means known to those of skill in the art. Addition of a methionine to the N-terminus of the peptides provided herein can be used as a target to generate a circularized peptide using the method of Tam and Xu (Biopolymers (1998) Methionine ligation strategy in the biomimetic synthesis of parathyroid hormones 46: 319-329). The peptides may have substituents bonded to either terminus of the peptide. For example, the peptide may have an acetyl or a carbamyl addition at the N-terminus, and/or an amide addition at the C-terminus. In addition, the peptides may be multimerized beyond a dimer, or circularized using standard chemistry to provide pharmacological stability. The multimers may contain more than one copy of one of the peptides disclosed herein or may contain inverse copies of a single peptide or more than one of the peptides disclosed herein. Those of skill in the art will appreciate that various additional modifications of the peptides provided herein may be made to increase the stability or half-life of the peptides in culture or in the subject after administration. For example fatty acids or other modifications may be added to the N-terminus including but not limited to formylation, myristoylation, or PEGylation. The peptide may be attached to a carrier protein to increase the stability of the peptide. The carrier protein-peptide may be a fusion protein and may be expressed as a recombinant protein using techniques available to those of skill in the art. The peptide bonds connecting the amino acids of the peptide may be altered or at least one peptide bond may be altered to make the peptides more resistant to degradation, for example a methyl group could be added. The amino acids could be replaced with functionally related non-natural amino acid that share similar side chains to the natural amino acid, such as replacement of the cysteine with homocysteine or α-methyl-cysteine.

Delivery particles may be used to deliver either DNA vaccines or peptide-based vaccines. The delivery particles may include any one of the compositions disclosed herein. Delivery particles suitable for delivering polynucleotides and/or proteins are known in the art and may include, without limitation, polymeric nanoparticles, liposomal nanoparticles, and nanoparticles including lipids and at least one type of polymer.

Polymeric Nanoparticles

Polymeric nanoparticles have been described in the art. (See, e.g., Reis et al., Nanomedicine 2 (I) (2006) 8-21; Kumari et al., Colloids and Surfaces B: Biointerfaces 75 (2010) 1-18; and U.S. Patent Publication 20140066388; the contents of which are incorporated herein by reference in their entireties). Polymeric nanoparticles may include or may be formed from biodegradable polymeric molecules, which in some embodiments may include dendrimers. Suitable dendrimers may include, but are not limited to, polyamidoamine (PAMAM) dendrimers. Polyamidoamine dendrimers have been used in the art as vehicles for intracellular delivery of therapeutics. (See Esfand et al., Drug Discov. Today (2001) 6(8):427-436; and Bharali, International Journal of Nanomedicine (2009) 4:1-7: the contents of which are incorporated herein by reference in their entireties). Polyamidoamine dendrimers suitable for preparing the presently disclosed nanoparticles may include 3rd-, 4th-, 5th-, or preferably at least 6th-generation dendrimers.

Polymeric nanoparticles may also include or may be formed from other biodegradable polymeric molecules which may include, without limitation, polylactic acid (PLA), polygycolic acid (PGA), co-polymers of PLA and PGA (i.e., polyactic-co-glycolic acid (PLGA)), poly-ε-caprolactone (PCL), polyethylene glycol (PEG), poly(3-hydroxybutyrate), poly(p-dioxanone), polypropylene fumarate, poly(orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis(p-carboxypheonoxy)methane](PCPM), copolymers of PSA, PCPP and PCPM, poly (amino acids), poly(pseudo amino acids), polyphosphazenes, derivatives of poly[(dichloro)phosphazenes] and poly[(organo)phosphazenes], poly-hydroxybutyric acid, or S-caproic acid, elastin, gelatin, and chitosan. (See. e.g., Kumari et al., Colloids and Surfaces B: Biointerfaces 75 (2010) 1-18; and U.S. Pat. Nos. 6,913,767; 6,884,435; 6,565,777; 6,534,092; 6,528,087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/0081972; and International Application Publication Nos. WO 2012/115806; and WO 2012/054425; the contents of which are incorporated herein by reference in their entireties). In some embodiments, the nanoparticles may include a mixture of PLGA and PAMAM.

Polymeric nanoparticles may be prepared by methods known in the art. (See, e.g., Nagavarma et al., Asian J. of Pharma. And Clin. Res., Vol 5, Suppl 3, 2012, pages 16-23; Cismaru et al., Rev. Roum. Chim., 2010, 55(8). 433-442; and International Application Publication Nos. WO 2012/115806; and WO 2012/054425; the contents of which are incorporated herein by reference in their entireties). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the nanoparticles may be prepared by forming a double emulsion (e.g., water-in-oil-in-water) and subsequently performing solvent-evaporation. The nanoparticles obtained by the disclosed methods may be subjected to further processing steps such as washing and lyophilization, as desired. Optionally, the nanoparticles may be combined with a preservative (e.g., trehalose).

Micelle and Liposomal Nanoparticles

Micelle and liposomal-based nanoparticles may also serve as suitable delivery particles. See. e.g., U.S. Pat. No. 8,252,324 the contents of which is incorporated herein by reference in its entirety. Micelles are self-assembling spherical colloidal nanoparticles formed by amphiphilic molecules. Micelles are also described as aggregate surfactant molecules disbursed in a liquid colloid. The core of the micelle, which is segregated in an aqueous milieu, is capable of encapsulating polynucleotides and/or proteins protecting them from destruction and biological surroundings while improving their pharmacokinetics and biodistribution. Micelles are generally in the order of 5-50 nm in diameter, and are therefore capable of accumulating in pathological areas with leaky vasculature, such as infarct zones and tumors due to the enhanced permeability and retention effect. Micelles are also capable of evading a major obstacle in drug targeting by particulate systems: non-specific uptake by the reticulo-endothelial systems and renal secretion.

Micelles may be formed by any of commonly known surfactants, such as sodium dodecylsulfate or phospholipids, but the performance of such surfactants as drug delivery systems is low compared to micelles composed of specially designed block copolymers, as described in Kataoka et al., supra and Torchilin et al., supra (2003). The flexible hydrophilic polymers, which are used as shell-forming segments for the polymer micelles, assemble into a dense palisade shell, which is cross-linked by numerous water molecules to achieve effective stabilization of the vesicle. Accordingly, the polymer micelles dissociate much more slowly than unmodified surfactant micelles, retain the loaded drugs for a longer period of time and accumulate the drug at the target site more efficiently. Further, polymer micelles are readily engineered to have sizes in the range of several tens of nanometers with a narrow size distribution which is a great advantage in regulating biodistribution.

In contrast to micelles, liposomes are bilayered phospholipid vesicles approximately 50 to 1,000 nm in diameter. Liposomes are biologically inert and completely biocompatible; they cause practically no toxic or antigenic reactions. Polynucleotides and/or proteins included in liposomes are protected from the destructive action of the external media by the liposomes. Thus, liposomes are able to deliver their content inside cells and even inside different cell compartments. Generally, liposomes are considered a promising carrier with significant therapeutic potential, as demonstrated in numerous laboratory tests and clinical trials, e.g., Torchilin. Nat. Rev. Drug discov. 4, 145-160 (2005).

It is known that liposomes and micelles can be stabilized by enhancing the outermost hydrophobic shell with water soluble polymers, such as polyethyleneglycol (PEG). The presence of hydrophilic polymers on the hydrophobic surface of these carrier particles attracts a water shell, resulting in reduced adsorption of opsonins to the carrier particles. This, in turn, results in a decrease in both the rate and extent of uptake of carrier particles by mononuclear phagocytes. Long circulating liposomes improved the therapeutic index of drugs and encapsulated therein. Currently, several preparations based on long circulating liposomes are commercially available, for example, Doxil®, a doxorubicin containing polyethyleneglycolated (PEGylated) liposomes, Sharp et al., Drugs 62 2089-2126 (2002). Doxil is manufactured by ortho biotech products. LP of Bridgewater, N.J., USA. O'Shaughnessy, Clin. Breast cancer 4, 318-328. (2003), demonstrated selective delivery of doxorubicin into solid tumors in patients with breast carcinoma metastases was achieved by capsulation of the drug into PEGylated liposomes, which resulted in subsequent improvement of survival. Efficacy was also demonstrated by combining liposomal doxorubicin with paclitaxel (available as Taxol®, Bristol-Meyers Squibb Company, New York, N.Y., USA) caelyx (Schering-Plough corporation, Kenilworth, N.J., USA) and carboplatin (available as Paraplatin® from Bristol-Meyers Squibb company). Several preparations of liposomes have been approved for clinical application or undergoing clinical evaluation, Torchilin, supra, (2005).

Exemplary delivery particles have also been disclosed in, for example, U.S. Patent Publication No. 20150232883 and WO Patent Publication Nos. 2014/093635 and 2015/089351; the contents of which are incorporated herein by reference in their entireties. In some embodiments, the delivery particles comprise 1,2-dioleoyl-3-trimethylammonium-propane (DOTAP), 1,2-ditetradecanoyl-sn-glycero-3-phosphocholine (DMPC), polyethylene glycol (PEG), cholesterol, or any combination thereof.

Nanoparticles Including Lipids and Polymers

Delivery particles may also include nanoparticles including lipids and polymer components. For example, nanoparticles including a phospholipid bilayer and poly(beta-amino ester) (PBAE) have been developed for the in vivo delivery of polynucleotides. See. e.g., Su et al., *Molecular Pharmaceutics*, 8(3):774-787 (2011); the contents of which is incorporated herein by reference in its entirety.

General Properties of Delivery Particles

The delivery particles may include a surfactant which may include a cationic surfactant. Suitable cationic surfactants may include but are not limited to quaternary ammonium compounds, for example, quaternary ammonium compounds or salts thereof having a formula $(X)_3N^+(CH_2)_n(CH_3)$ where X is $C_{1-6}$ alkyl or aryl, and n=(9, 11, 13, 15, or 17). Suitable salts of the quaternary ammonium compounds may include halide salts (e.g., $Cl^-$ or $Br^-$ salts) such as cetyltrimethylammonium bromide (CTAB).

The delivery particles preferably have physical properties that facilitate uptake by a targeted cell. For example, preferably the nanoparticles have a size and a charge that that facilitate uptake by a targeted cell. Typically, the nanoparticles have a mean effective diameter of less than 1 micron, and preferably the nanoparticles have a mean effective diameter of between about 25 nm and about 500 nm, and more preferably between about 50 nm and about 250 nm, and most preferably about 100 nm to about 150 nm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM), Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

The disclosed delivery particles preferably have a zeta-potential that facilitates uptake by a target cell. Typically, the nanoparticles have a zeta-potential greater than 0. In some embodiments, the nanoparticles have a zeta-potential between about 5 mV to about 45 mV, between about 15 mV to about 35 mV, or between about 20 mV and about 30 mV. Zeta-potential may be experimental determined via characteristics that include electrophoretic mobility or dynamic electrophoretic mobility. Electrokinetic phenomena and electroacoustic phenomena may be utilized to calculate zeta-potential.

Delivery particles will be taken up by cells non-specifically even if the particles do not include a specific ligand on their surface. However, the disclosed delivery particles may be configured to also include a ligand that specifically targets a particular cell type. In order to achieve more specific targeting of delivery particles, such particles may be modified with various ligands using advance conjugation procedures. For example, antibodies and small peptides have been attached to the water exposed tips of polyethyleneglycol chains, Blume, et al. Biomembranes 1149, 180-184 (1993). Antibodies and small peptides have also been conjugated via reactive p-nitrophenylcarbonyl, N-benzotrazole carbonyl or maleimide terminated PEG-phosphatidylethanolamine, Moreira, Pharm. Res. 19, 265-269 (2002); Torchilin et al., supra (2001); Xiong, et al., J. Pharm. Sci. 94, 1782-1793 (2005).

The vaccine formulations described herein may be combined with adjuvants to increase immunogenicity of the vaccine and derive pharmaceutical compositions. In some embodiments, these compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of Quillaja *saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum*, *C. granulosum*, *Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein. Notably, several of the delivery particles noted above may also act as adjuvants.

In some embodiments, compositions further comprise cytokines (e.g. IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans). In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496 the contents of which are hereby incorporated by reference in their entireties.

In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, compositions comprise oil-in-water emulsion formulations, saponin adjuvants, ovalbumin, Freunds Adjuvant, cytokines, and/or chitosans. Illustrative compositions comprise one or more of the following.

(1) ovalbumin (e.g. ENDOFIT);

(2) oil-in-water emulsion formulations, with or without other specific immunostimulating agents, such as: (a) MF59 (PCT Publ. No. WO 90/14837), which may contain 5% Squalene, 0.5% Tween 80, and 0.5% Span 85 (optionally containing various amounts of MTP-PE) formulated into submicron particles, (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, Mo.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+ CWS (DETOX™); and (d) ADDAVAX (Invitrogen);

(3) saponin adjuvants, such as STIMULON (Cambridge Bioscience, Worcester, Mass.);

(4) Complete Freunds Adjuvant (CFA) and Incomplete Freunds Adjuvant (IFA);

(5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc;

(6) chitosans and other derivatives of chitin or poly-N-acetyl-D-glucosamine in which the greater proportion of the N-acetyl groups have been removed through hydrolysis; and (7) other substances that act as immunostimulating agents to enhance the effectiveness of the composition, e.g., monophosphoryl lipid A.

In other embodiments, adjuvants include a flagellin-based agent, an aluminium salt or gel, a pattern recognition receptors (PRR) agonist, CpG ODNs and imidazoquinolines. In some embodiments, adjuvants include a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

Methods of treating a cancer or pre-cancer, or of reducing the likelihood of the cancer or pre-cancer developing resistance to a cancer therapeutic or prevention agent, are also provided. The methods include administering the vaccine formulations as described above to a subject having cancer or pre-cancer. The subject may be any mammal, suitably a human, domesticated animal such as a dog, cat, horse, cow, pig, or a mouse or rat. A cancer therapeutic or prevention agent may be administered concurrently with, before or after administration of the vaccine.

The methods may also include administering to the subject a therapeutically effective amount of a DNA vaccine and administering to the subject a therapeutically effective amount of a vaccine vector composition. Preferably, the DNA vaccine includes a first polynucleotide encoding a first antigenic polypeptide and the vaccine vector composition includes a second antigenic polypeptide. The first antigenic polypeptide and the second antigenic polypeptide may be the same polypeptide or fusion polypeptide or may be different polypeptides or fusion polypeptides. The DNA vaccine may be administered prior to, during, or after administration of the vaccine vector composition. In some embodiments, the DNA vaccine is administered at least 2, 3, 4, 5, or more times prior to administration of the vaccine vector composition. The time period between administration of the DNA vaccine and the vaccine vector composition may be at least 1, 2, 3, 4, 5 week(s) or more.

The cancer therapeutic or prevention agents may be any agent capable of treating the cancer or inhibiting growth of cancer cells. Suitable agents include those which target HER2, HER1/EGFR, HER3, estrogen receptor or IGF1R. The therapeutic agent may be trastuzumab (Herceptin), ado-trastuzumab emtansine, lapatinib, pertuzumab or another HER2 targeting therapeutic agent or it may be an EGFR targeting therapeutic agent such as cetuximab, gefitinib, panitumumab or erlotanib, or it may be an anti-estrogen, or an agent that prevents estrogen synthesis such as an aromatase inhibitor. ER-positive cancers may also be treated with Palbociclib or Everolimus. We have previously demonstrated that a HER3 vaccine can treat a HER2 positive cancer when used in combination with a therapeutic agent targeting HER2. Cancer cells often develop resistance to HER2 targeting therapeutic agents. Addition of vaccination with a HER2, HER3 or ESR1 vaccine or passively transferred polyclonal antibodies specific for HER2, HER3 or ESR1 resulted in blocking resistance, inhibited cancer cell growth and resulted in treatment of the cancer.

Suitably the vaccinated subject develops an immune response to the antigenic polypeptide used in the vaccine formulation in response to administration of the vaccine. The immune response may be an antibody or T cell immune response. For example the immune response may include antibody-dependent cellular cytotoxicity, polyclonal antibody response, complement dependent cellular cytotoxicity, cellular cytotoxicity, disruption of ligand binding, disruption of dimerization, mimicking ligand binding causing internalization of the target antigen, or degradation of the targeted antigen. The immune response may comprise an antibody response directed to at least a portion of the targeted antigen, suitably a portion including the mutation site or an overexpressed and accessible portion of the antigen. The immune response may be specific for a T cell or B cell epitope flanking or encompassing the deletion of exon 16 at amino acid 633 of SEQ ID NO: 3 for example or regions flanking the deletion of exon 16 in HER2d16.

Reduction of the development of resistance can be measured in several ways. The resistance of the vaccinated subject may be compared to a similar subject that was not vaccinated as in the Examples. Alternatively, the reduction may be measured based on statistics generated regarding the likelihood of an individual being treated with the therapeutic agent to develop resistance versus that of individuals treated with the therapeutic agent and vaccinated with one or more of the vaccine formulations provided herein. The reduction in the likelihood of resistance of the cancer may also be measured by measuring the level of antigen expression on the surface of cancer cells. HER2, HER3 and ESR1 expression is reduced on cancer cells after effective administration of the vaccine. The effectiveness of the vaccine in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The cancer may be selected from any cancer capable of developing resistance to a therapeutic agent by increasing expression or activation of a protein by the cancer cells. In particular the cancer may be any cancer capable of developing resistance to a therapeutic agent which targets a HER family tyrosine kinase, suitably HER2, HER3, or EGFR or the estrogen receptor, suitably anti-estrogens. The cancer may develop resistance by increasing the expression of HER2, HER3 or ESR1, deleting a portion of HER2 or mutating ESR1 to avoid susceptibility to the therapeutic agent. Suitably the cancers are selected from breast, prostate, lung, ovarian, colon, rectal, pancreas, bladder, head and neck or liver cancers or pre-cancers.

The resistance may be due to a single or multiple changes, and the vaccine formulations or vaccination protocol can target one or more of these changes, and/or include multiple antigens likely found in resistant cells, but not necessarily in all resistant cells.

Treating cancer includes, but is not limited to, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

Co-administration, or administration of more than one composition (i.e. more than one vaccine formulation, therapeutic agents and/or checkpoint inhibitory immunomodulatory agents) to a subject, indicates that the compositions may be administered in any order, at the same time or as part of a unitary composition. The compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more. In the Examples, the two vaccine formulations were administered at two week intervals for a total of two or three vaccinations and may be combined with a checkpoint inhibitory immunomodulatory agent.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e., the vaccine formulations including the delivery particles and the therapeutic agents or checkpoint inhibitory agents) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intra-lesional, intra-tumoral, intradermal, or transmucosal absorption. Thus the compositions may be formulated as an ingestable, injectable, topical or suppository formulation. The compositions may also be delivered with in a liposomal or time-release vehicle. The DNA and polypeptide vaccines may also include an electrical stimulation or electroporation step to aid entry of the DNA vaccine or peptide based vaccine into the intracellular space. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce the growth of the cancer at least 10%, 20%, 30%, 40%, 50%, 60%, 70%, 80%, 90%, 100% or more as compared to no treatment or treatment with only the therapeutic agent. It is specifically contemplated that pharmaceutical preparations and compositions may palliate, block further growth or alleviate symptoms associated with the cancer without providing a cure, or, in some embodiments, may be used to cure the cancer and rid the subject of the disease.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The vaccine formulations may be administered one time or more than one time to the subject to effectively boost the immune response against the antigenic polypeptide. If the vaccine formulation is provided as a vaccine vector, the vaccine vector may be administered based on the number of particles delivered to the subject (i.e. plaque forming units, colony forming units, liposomes or other particles). The subject may be administered $10^{12}$, $10^{11}$, $10^{10}$, $10^9$, $10^8$, $10^7$ or $10^6$ particles. The amount of antigenic polypeptide delivered in a delivery particle based peptide vaccine formulation or DNA vaccine will vary. Suitable dosage ranges are of the order of several hundred micrograms effective ingredient (antigenic polynucleotide or polypeptide) per vaccination with a range from about 0.01 to 10 mg/kg/day, preferably in the range from about 0.1 to 1 mg/kg/day. Suitable regiments for initial administration and booster shots are also variable but are typified by an initial administration followed by subsequent inoculations or other administrations with a period of time between administrations. Precise amounts of effective ingredient required to be administered depend on the judgment of the practitioner and may be peculiar to each subject. It will be apparent to those of skill in the art that the therapeutically effective amount of antigenic polypeptide expressing DNA constructs or antigenic peptides described herein will depend, inter alia, upon the administration schedule, the unit dose of antigen administered, whether the vaccine formulation is administered in combination with other therapeutic agents, the immune status and health of the recipient, and the therapeutic activity of the particular vaccine formulation.

The compositions can be given in a single dose schedule, or preferably in a multiple dose schedule. A multiple dose schedule is one in which a primary course of vaccination can include 1 to 10 separate doses, followed by other doses given at subsequent time intervals required to maintain and or reinforce the immune response, for example, at 1 to 4 weeks or months for a second dose, and if needed, a subsequent dose(s) after several additional weeks or months. Periodic boosters at intervals of 1 to 5 months to years, may be desirable to maintain the desired levels of immune responsiveness.

Cancer vaccine kits are also provided. The cancer vaccine kits may include a DNA vaccine component including a first polynucleotide encoding a first antigenic polypeptide and a vaccine vector component including a second antigenic polypeptide. Suitably, the DNA vaccine component includes any one of the polynucleotide constructs described herein. The first antigenic polypeptide and the second antigenic polypeptide may be the same polypeptide or fusion polypeptide or may be different polypeptides or fusion polypeptides.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

Materials and Methods

Reagents

Mixtures of HER3 peptides containing 15mer peptides, each overlapping the next by 11 amino acids, spanning extracellular domain plus transmembrane segment (ECD-TM) of HER3 protein and intracellular domain (ICD) of HER3 protein, were purchased from JPT Peptide Technologies (Berlin, Germany), and were used for the IFN-γ ELISPOT assay. An HIV peptide mix representing HIV gag protein was purchased from BD Biosciences (San Jose, Calif.) and was used as a negative control.

Construction and Production of hHER3ECDC1C2 Minicircle DNA

The extracellular domain of human HER3 obtained by PCR technique from human HER3 cDNA (OriGene, Rockville, Md.) was inserted into the mouse Lactadherin expression plasmid p6MLC1C2 (1) to create exosomal cassettes containing C1C2 domain of mouse lactadherin fused in-frame (hHER3ECDmC1C2). hHER3ECDmC1C2 DNA (SEQ ID NO: 11 and SEQ ID NO: 12, nucleic acid and amino acid sequences, respectively) was subcloned into minicircle parental plasmid (MN501A-1, System Biosciences, Mountain View Calif.). FIG. 7 provides a map of the plasmid. The resultant plasmid was further propagated and screened in Top10 E. coli competent cell. Positive clones were confirmed by restriction enzyme as well as DNA sequencing, and transformed into ZYCY10P3S2T E. coli minicircle producer strain (MN900A-1, SBI). The 100 ml (OD600 6-8) of overnight bacterial growth from a single colony of plasmid-transformed ZYCY10P3S2T was added to 200 ml fresh medium containing 1% L-arabinose (Sigma Chemical Co. St. Louis, Mo.), then incubated at 30° C. for 5 hr with shaking at 250 rpm. The minicircle DNA was prepared from bacteria using plasmid purification kits from t Qiagen (Germantown Md.). The quality of minicircie was checked by running agarose gel, the genomic and parental plasmid DNA contamination were by Minicircle-safe DNase (MN912A-1, SBI).

Construction and Production of pINGhHER3FL/pING-hHER3ECDC1C2

Human HER3 full length cDNA (OriGene, Rockville, Md.) or hHER3ECDmC1C2 DNA were cloned into pING-DNA vaccine vector designed to drive HER3 full length or human HER3ECDC1C2 fusion protein expression with a strong viral promoter (2). The pING parental vector contains the following elements: (i) a eukaryotic promoter and enhancer from the Towne strain of CMV; (ii) a polylinker region to facilitate cloning; (iii) donor and acceptor splice sites and a poly adenylation signal sequence derived from the bovine growth hormone gene; (iv) the ColE1 origin of replication and (v) a gene conferring kanamycin resistance. The resultant plasmid was further propagated and screened in Df5α E. coli competent cells. Positive clones were confirmed by restriction enzyme and DNA sequencing. The overnight bacterial growth from a single colony was used for the extraction of plasmids. The plasmid DNA was prepared from bacteria using plasmid purification kits from Qiagen.

Construction and Production of Ad-hHER3FL/Ad-hHER3ECDC1C2

The human HER3 full length and hHER3ECDC1C2 DNA were subcloned and ligated directionally into the pShuttle CMV plasmid multiple cloning sites (See, e.g., FIG. 1). The resultant plasmid thus places the CMV-HER3FL/HER3ECDC1C2-polyA mini-gene cassette within the E1 region of the Ad5 genome. Homologous recombination with the pAdEASY Δpol, ΔpTP plasmid under Kanamycin selection resulted in the isolation of the plasmid pAdCMV/HER3FL/Δpp. The plasmids contain Ad5 genome deleted for the E1, polymerase, pTP and E3 genes. PacI digestion of the pAdCMV/HER3FL/Δpp plasmid releases the vector genome from bacterial plasmid sequences, and transfection of this ~33kb plasmid into the C7 cell lines yields the final virus: Ad5 [E1-, E2b-]-HER3FL or Ad5 [E1-, E2b-]-HER3ECDC1C2.

Mice

Female wild-type BALB/c mice (Jackson Laboratory, Bar Harbor, Me., USA) were bred and maintained in the Duke University Medical Center pathogen-free Animal Research Facility, and used at 6 to 8 weeks of age. Human HER3-transgenic mice (MMTV-neu/MMTV-hHER3) with FVB background were a kind gift from Dr. Stan Gerson at Case Western Reserve University. FVB mice homozygous for the HER3 gene were established at Duke University and crossed with BALB/c mice to generate F1 hybrid HER3 transgenic mice (FVB×BALB/c) for use in tumor implantation experiments. All animal studies described were approved by the Duke University Medical Center Institutional Animal Care & Use Committee, in accordance with guidelines published by the Commission on Life Sciences of the National Research Council.

IFN-γ Enzyme-Linked Immunosorbent Spot (ELISpot) Assay

Mouse IFN-γ ELISPOT assay (Mabtech Inc., Cincinnati, Ohio) was performed according to the manufacturer's instructions. At the end of the mouse experiments, their spleens were collected and lymphocytes were harvested by mincing and passing through a 40 μm Cell Strainer. Red blood cells were lysed with red blood cell lysis buffer (Sigma). Splenocytes (500,000 cells/well) were incubated in RPMI-1640 medium (Invitrogen) supplemented with 10% horse serum, and HER3 ECD-TM peptide mix and/or HER3 ICD peptide mix (1.3 μg/ml) were used as stimulating antigens. HIV peptide mix was used as a negative control, and a mixture of PMA (50 ng/ml) and Ionomycin (1 μg/ml) was used as a positive control for the assay. Membranes were read with a high-resolution automated ELISpot reader system (Carl Zeiss, Inc., Thornwood, N.Y., USA) using the KS ELISpot version 4.2 software.

Flow Cytometric Analysis of Anti-HER3 Antibody

When mice were euthanized, blood was collected and isolated serum was frozen stocked at −80 C until the time of the assay. 4T1 cells were transduced with HER3 gene by lentiviral vectors to express human HER3 on the cell surface (4T1-HER3 cell). Both 4T1 parental cells and 4T1-HER3 cells were incubated with diluted mouse serum (1:100) for 30 min on ice, washed with PBS, and then co-incubated with PE-conjugated anti-mouse IgG secondary antibody (1:200) for 30 min on ice. After washing with PBS twice, cells were acquired by LSRII machine (BD Biosciences, San Jose, Calif.) to analyze the presence of HER3 specific antibody in the serum.

Cell-Based ELISA for Anti-HER3 Antibody

4T1 cells were transduced with HER3 gene by lentiviral vectors to express human HER3 on the cell surface (4T1-HER3 cell). 4T1 and 4T1-HER3 cells were put into 96 well flat bottomed plates (3×10E4 cells/100 μL medium/well) the day before the assay and incubated overnight at 37° C. Mouse sera were prepared by diluting with DMEM medium (final titrations 1:50~1:6,400), and 50 μl of mouse sera containing media were added to the wells and incubated for 1 hour on ice. The plates were gently washed with PBS twice, and then, cells were fixed with diluted Formalin (1:10 dilution of Formalin in 1% BSA in PBS), incubated for 20 min at room temperature. After three times wash with PBS, 50 μL of 1:2000 diluted HRP-conjugated goat anti-mouse IgG was added to the wells, and incubated for 1 h at room temperature. After three times wash with PBS, TMB substrate was added to the wells (50 μL/well) and incubated for approximately 20 min. The color development was stopped by adding 50 μL of 1M $H_2SO_4$ buffer. Absorbance at 450 nm was read using BioRad Plate Reader (Model 680). As the alternative method for the detection of antibody, near infrared (nIR) dye-conjugated anti-mouse IgG (IRDye 800CW, LI-COR Biosciences, Lincoln, Nebr.) was used as a secondary antibody, and the nIR signal was detected by LI-COR Odyssey Imager at 800 nm channel and analyzed using Image Studio software (LI-COR).

Vaccination of Mice with Minicircle DNA and Plasmid DNA

Mice were anesthetized with ketamine/xylatine/atropine, and minicircle DNA (mcDNA-HER3/ECD-mC1C2, mcDNA-HER3-FL) or plasmid DNA (pDNA-HER3/ECD-mC1C2, pDAN-HER3-FL) in 50 μl of saline was injected into the Tibialis Anterior muscle. Soon after injection, in vivo electroporation (50 V, 5 pulses, pulse length 60 ms, interval time 200 ms) was given to the leg using BTX ECM830 Electroporator (Harvard Apparatus, Holliston, Mass.). Electroporation was repeated to each mouse by placing the tweezer type electrode perpendicularly from the 1st position.

Vaccination of Mice with Adenovirus Vector

Under general anesthesia, Adenovirus encoding hHER3/ECD-C1C2 (2.6×10E10 viral particles/40 μl/injection), were injected to bilateral footpads (20 μl for each foot pad, total 40 μl/mouse) of mice.

Prophylactic Anti-Tumor Model in HER3 Transgenic Mice

HER3 transgenic F1 hybrid mice were immunized by intramuscular injection of minicircle DNA (mcDNA-HER3/ECD-mC1C2) or plasmid DNA (pDNA-HER3/ECD-mC1C2) followed by electroporation using BTX ECM830. Immunization with adenovirus was performed by injection of the Ad[E1-,E2b-]-HER3/ECD-mC1C2 ($2.6×10^{10}$ particles in 40 μL of saline) to bilateral footpads. One week after the final vaccination, mice were inoculated with $5×10^5$ JC-HER3 cells (Experiment 1) or $3×10^5$ 4 T1-HER3 cells (Experiment 2) in 100 μL saline subcutaneously into the flank. Tumor dimensions were measured serially, and tumor volumes calculated using the following formula: long axis x (short axis)×0.5.

Results

Immunogenicity Test: Comparison of Homologous Vaccine Vs. Heterologous Prime Boost Vaccine with mcDNA and Adenovirus Encoding hHER3/ECD-C1C2.

On day 0, HER3 Transgenic mice received vaccination by intramuscular injection of minicircle DNA encoding hHER3/ECD-C1C2 (25 μg/mouse) to the tibialis anterior muscle. Soon, in vivo electroporation was performed. As a negative control, saline was administered into the muscle. For comparison with mcDNA based vaccine, mice were vaccinated with Ad-HER3 virus via footpad injection (2.6× 10E10 vp/mouse). Mice were vaccinated once or three times on days 0, 14 and 28 (2 week interval) as shown in Table 1 below. Two weeks after the final vaccination, mice were euthanized, and spleen and blood were collected from individual mice. Cellular and humoral immune response against HER3 antigen was tested by IFN-gamma ELISPOT assay (See FIG. 2) and Cell-based ELISA (See FIG. 3), respectively.

TABLE 1

Vaccine Schedule Ad: Ad-HER3/ECD-C1C2
(2.6 × 10E10 vp/inj), mcDNA: minicircle
DNA-HER3/ECD-C1C2 (25 µg/inj)

| Group | Number of Mouse | Priming (Day 0) | Boost #1 (Day 14) | Boost #2 (Day 28) |
|---|---|---|---|---|
| 1 | 4 | Ad | saline | saline |
| 2 | 4 | Ad | Ad | Ad |
| 3 | 4 | saline | saline | Ad |
| 4 | 4 | mcDNA | Ad | Ad |
| 5 | 4 | mcDNA | mcDNA | Ad |
| 6 | 4 | mcDNA | mcDNA | mcDNA |
| 7 | 4 | saline | saline | saline |

Figure 2:
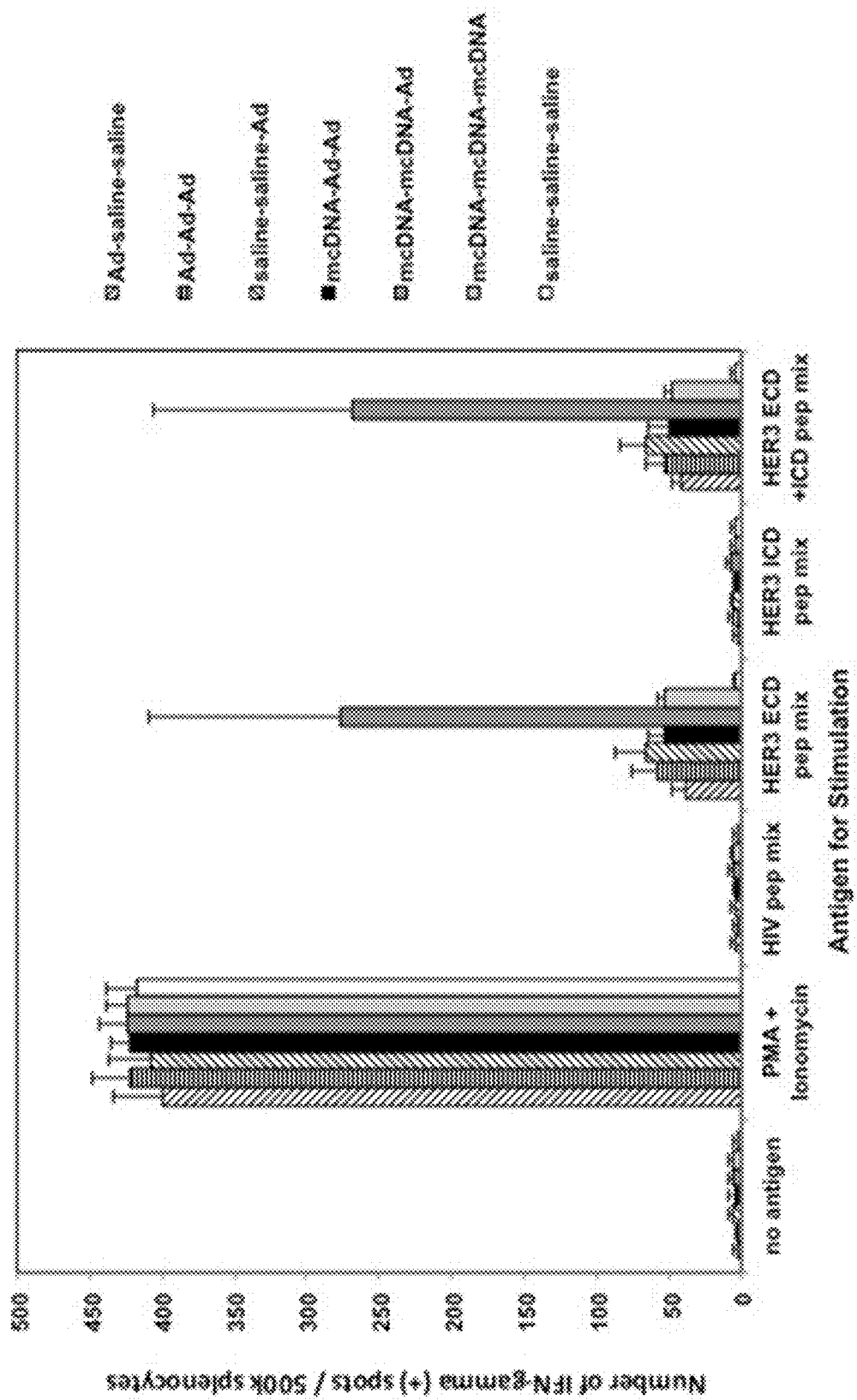
FIG. 2 shows IFN-gamma ELISPOT data. HER3 transgenic mice were vaccinated with footpad injection of Ad-hHER3/ECD-C1C2, or intramuscular injection of minicircle DNA-hHER3/ECD-C1C2 followed by in vivo electroporation (50V, 5 pulses, pulse length 60 ms, interval time 200 ms). Vaccinations were done for 3 times with 2 week intervals. Two weeks after the final vaccination, mice were sacrificed and IFN-gamma ELISPOT assay was performed with splenocytes. HER3 ECD peptide mix and/or HER3 ICD peptide mix were used as stimulating antigens. Each bar shows the average value for each arm. Error Bar: SD.

Importantly, repeated vaccinations with minicircle DNA-HER3/ECD-C1C2, followed by Ad-HER3/ECD-C1C2 induced significantly stronger cellular immune response against HER3 ECD antigen (FIG. 2). Repeat of Ad-HER3 alone or repeat of minicircle DNA-HER3/ECD-C1C2 alone induced anti-HER3 cellular response, but in similar level with Ad-HER3 single vaccination based on ELISPOT assay result. For the generation of humoral immune response, cell-based ELISA (FIG. 3A) showed that minicircle DNA-HER3/ECD-C1C2 followed by Ad-HER3/ECD-C1C2 could induce the strongest anti-HER3 antibody production, followed by repeat of Ad-HER3 vaccines for 3 times or mcDNA-HER3/ECD-C1C2 vaccine followed by repeat of Ad-HER3 vaccines. Thus, based on this immunogenicity test, mcDNA-HER3/ECD-C1C2 vaccine twice, followed by Ad-HER3/ECD-C1C2, appears to induce much enhanced anti-HER3 cellular and humoral immune response.

To confirm the strong antitumor effect induced by HER3-targeting heterologous prime-boost vaccine, here we demonstrate the stronger antitumor effect with this strategy compared to homologous prime-boost vaccines as shown below. We also tested the heterologous prime-boost vaccine utilizing plasmid DNA encoding HER3/ECD-C1C2 and Adenovirus.

Immunogenicity and Antitumor Efficacy Test: Heterologous Prime Boost Vaccine with mcDNA/pDNA and Adenovirus encoding hHER3/ECD-C1C2.

On day 0, HER3 Transgenic mice received vaccination by intramuscular injection of minicircle DNA or plasmid DNA encoding hHER3/ECD-C1C2 (25 µg/mouse, 50 µg/mouse, respectively) to the tibialis anterior muscle. Soon in vivo electroporation was performed. As a negative control, Ad-GFP vector (2.6×10E10 vp/mouse) was administered to footpad. For comparison with mcDNA or pDNA based vaccine, mice were vaccinated with Ad-HER3 virus via footpad injection (2.6×10E10 vp/mouse). Mice were vaccinated once or three times on days 0, 14 and 28 (2 week interval) as shown in Table 2 below.

TABLE 2

Vaccine Schedule Ad-HER3/ECD-C1C2 or Ad-GFP
(2.6 × 10E10 vp/inj) was injected to the bilateral
footpads. mcDNA-HER3/ECD-C1C2 (25 µg/inj) or
pDNA-HER3/ECD-C1C2 were intramuscularly
injected to the right tibialis anterior muscle, followed by
in vivo electroporation. Boosting was done for left tibialis
anterior muscle.

| Group | Number of Mouse | Priming (Day 0) | Boost #1 (Day 14) | Boost #2 (Day 28) |
|---|---|---|---|---|
| 1 | 10 | Ad-GFP | Ad-GFP | Ad-GFP |
| 2 | 10 | Ad-hHER3 | Ad-hHER3 | Ad-hHER3 |
| 3 | 10 | mcDNA | mcDNA | Ad-hHER3 |
| 4 | 10 | pDNA | pDNA | Ad-hHER3 |

Figure 3B:
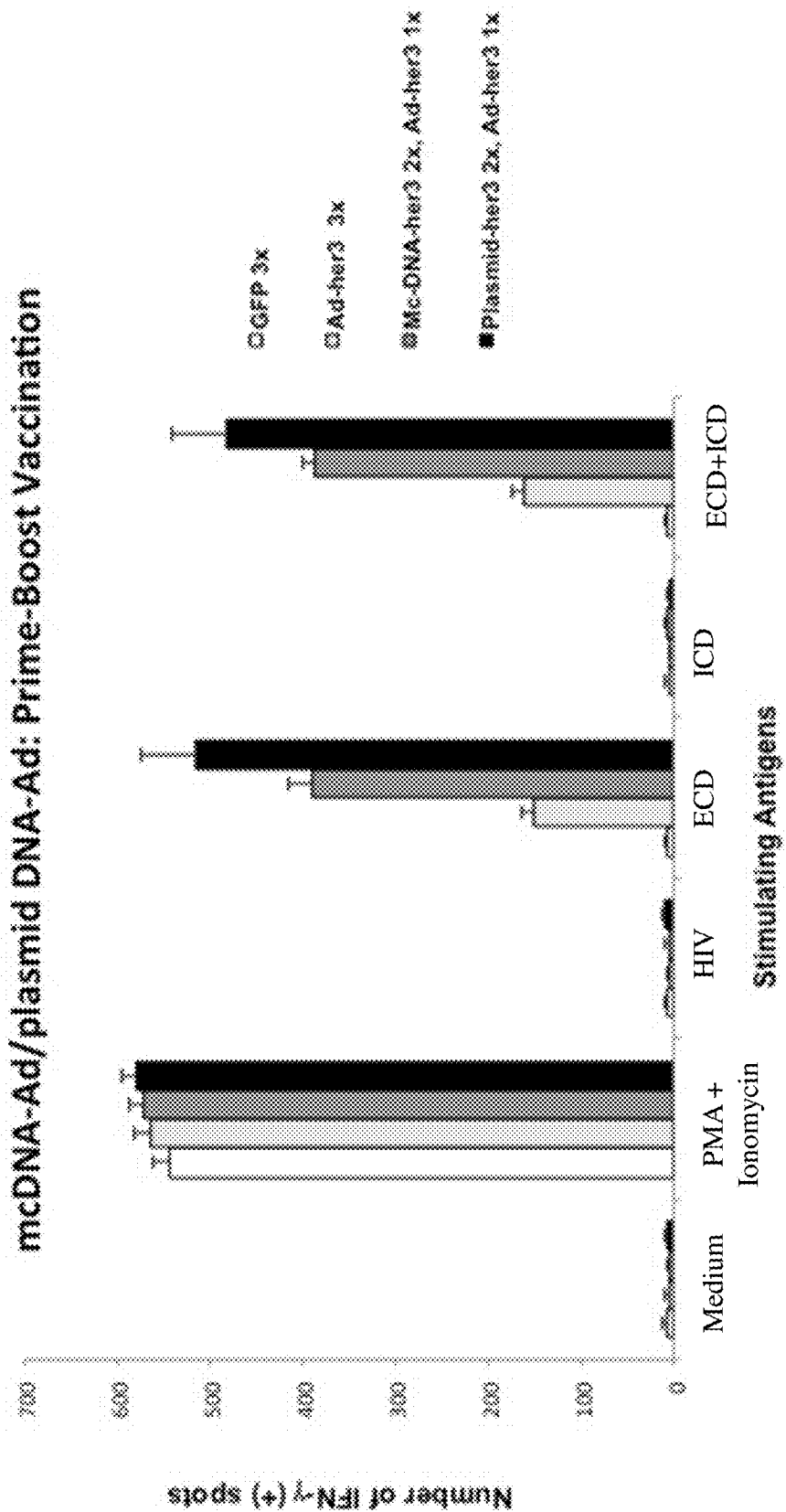
FIG. 3B shows IFN-gamma ELISPOT assay data. Mice were vaccinated with Ad-HER3/ECD-C1C2 for 3 times, or with heterologous prime-boost (mcDNA-HER3/ECD-C1C2×2 followed by Ad-HER3, or pDNA-HER3/ECD-C1C2×2 followed by Ad-HER3). Spleens were collected 7 days after the final vaccination and IFN-gamma ELISPOT assay was performed using HER3 ECD and ICD peptide mix as stimulating antigens. HER3 ECD peptide mix and/or HER3 ICD peptide mix were used as stimulating antigens.
Figure 4:
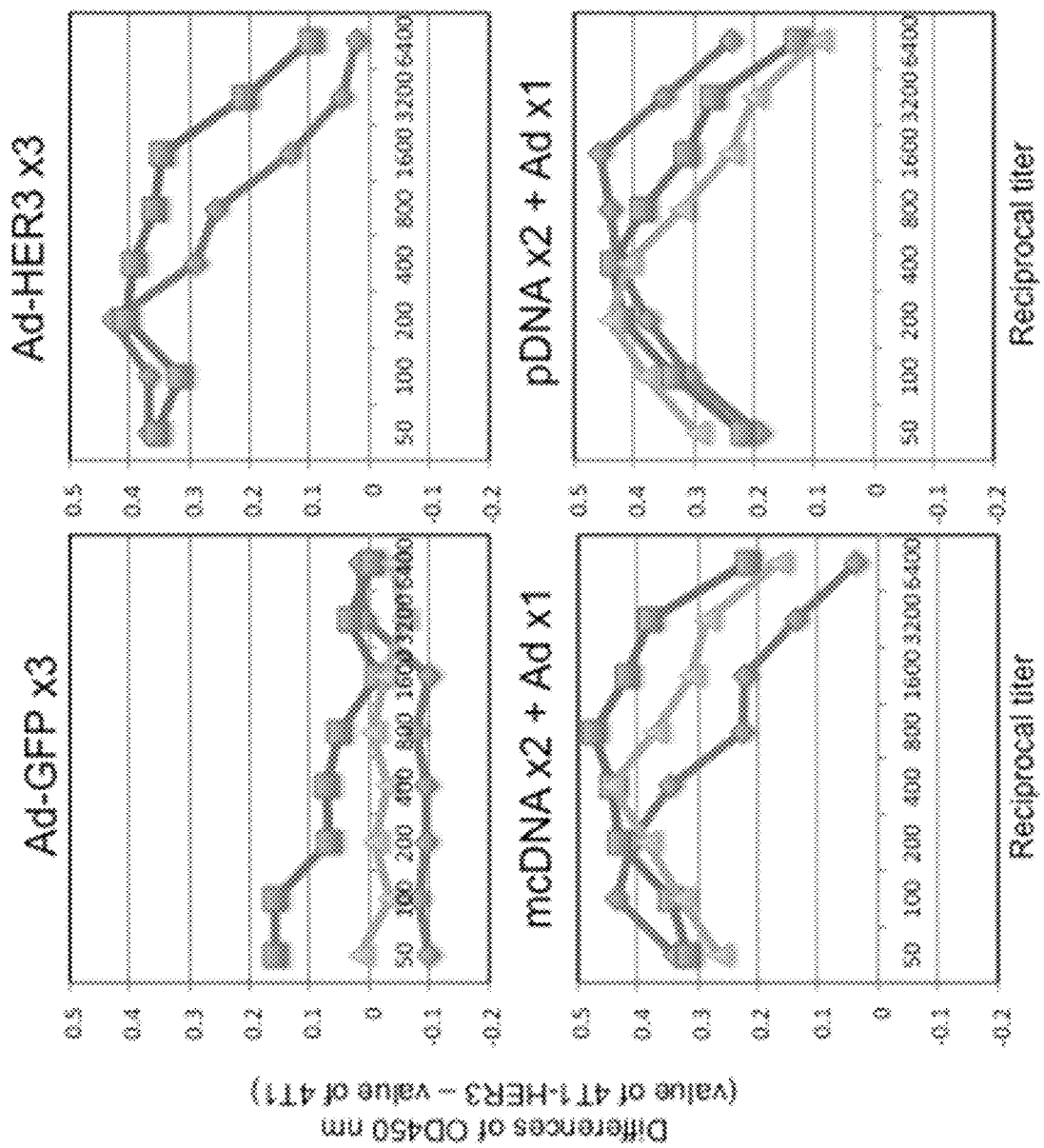
FIG. 4 shows cell-based ELISA data for anti-HER3 antibody (after vaccination). Mice were vaccinated with Ad-HER3/ECD-C1C2 for 3 times, or with heterologous prime-boost (mcDNA-HER3/ECD-C1C2×2 followed by Ad-HER3, or pDNA-HER3/ECD-C1C2×2 followed by Ad-HER3). Mice were sacrificed 7 days after the final vaccination, and blood was collected and Cell-based ELISA was performed with the serum.
Figure 5:
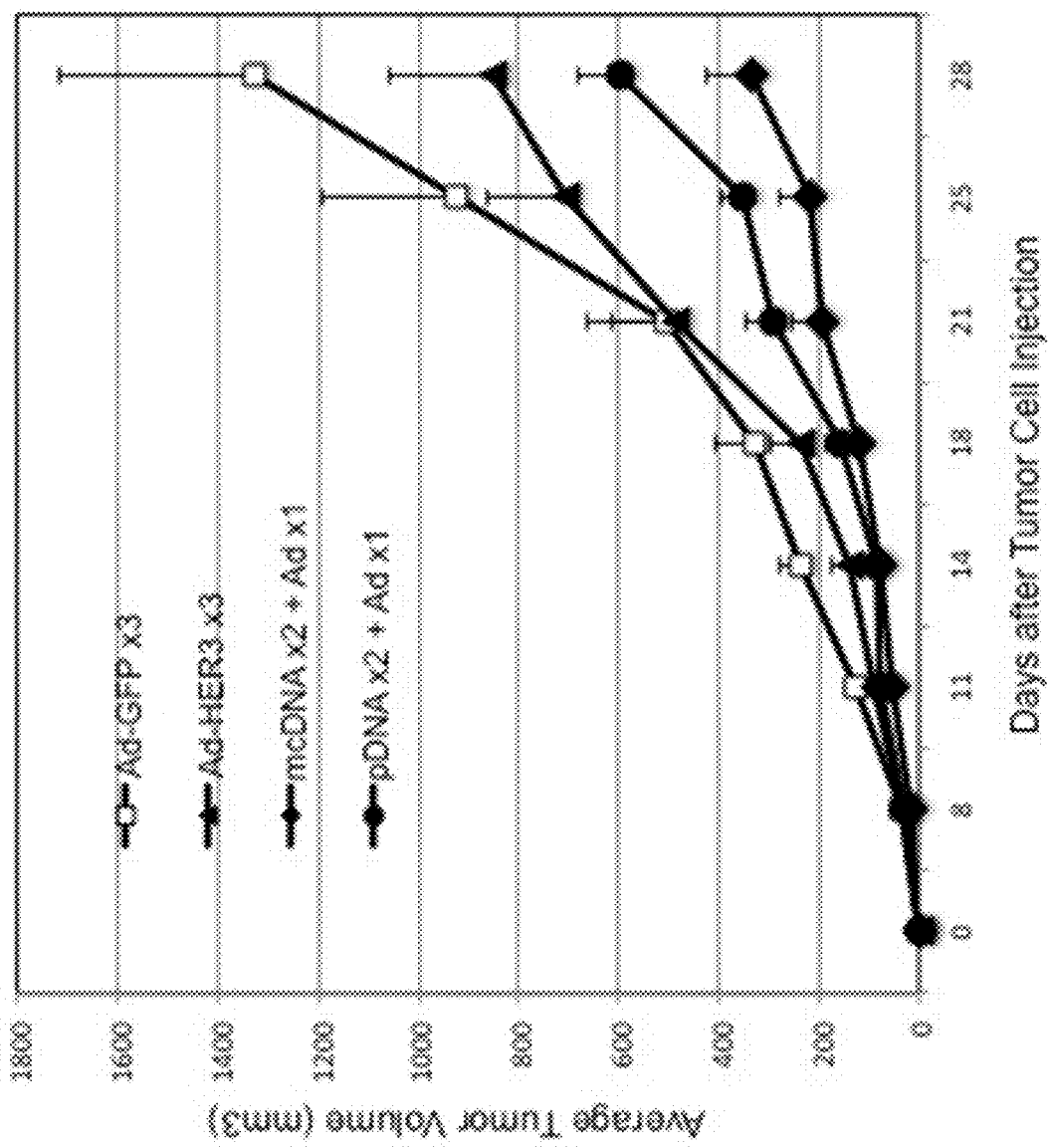
FIG. 5 shows 4T1-HER3 tumor growth in HER3 vaccinated mice. Mice were vaccinated with Ad-HER3/ECD-C1C2 for 3 times, or with heterologous prime-boost (mcDNA-HER3/ECD-C1C2×2 followed by Ad-HER3, or pDNA-HER3/ECD-C1C2×2 followed by Ad-HER3). Seven days after the final vaccination, 4T1-HER3 cells (0.3 M cells/mouse) implanted to the flank of mice, and tumor size was measured twice a week. Mice were sacrificed on day 28.
Figure 6:
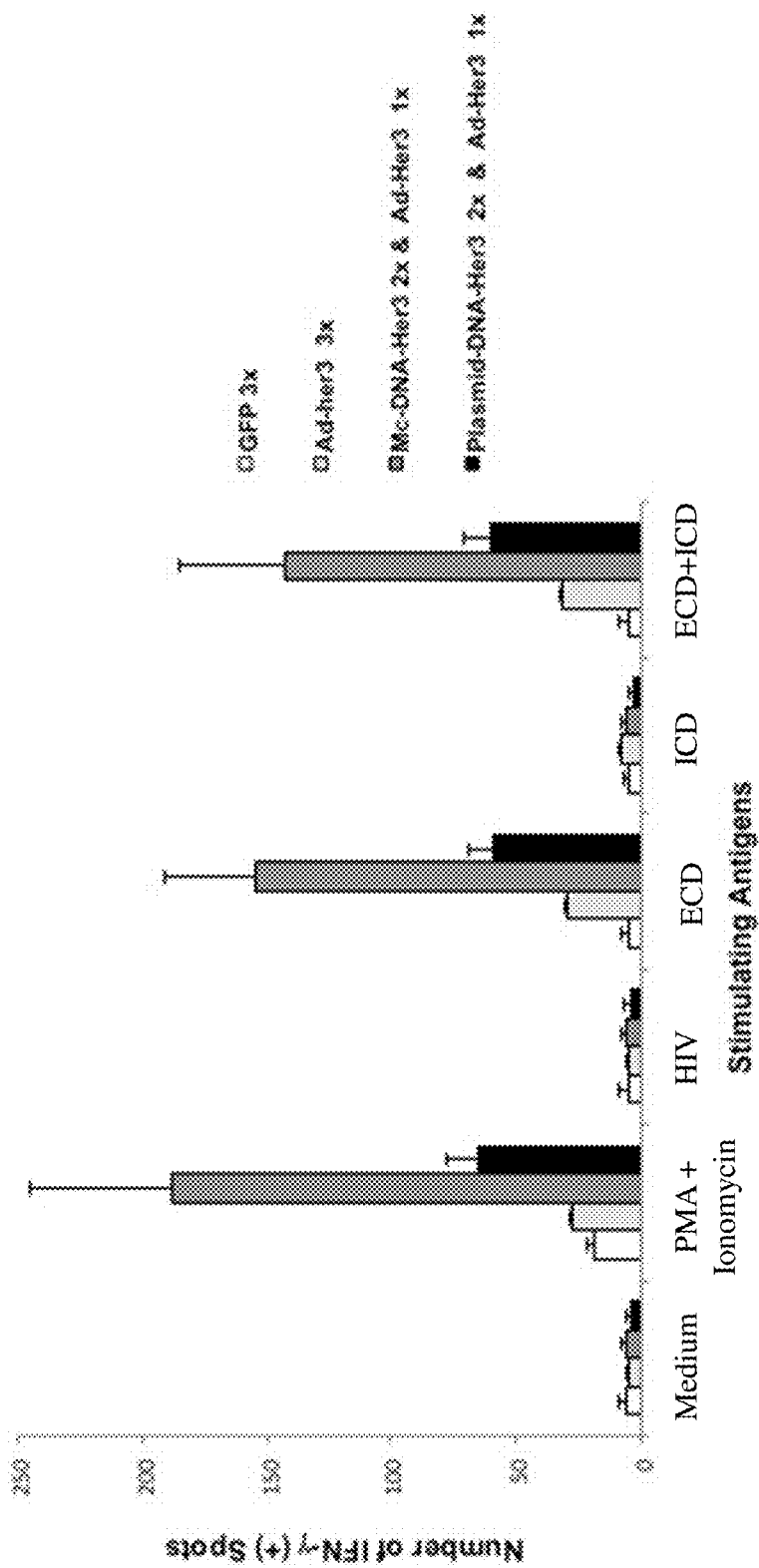
FIG. 6 shows IFN-gamma ELISPOT assay data at the end of experiment. After vaccination of mice with Ad-HER3/ECD-C1C2 for 3 times, or with heterologous prime-boost, 4T1-HER3 cells (0.3 M cells/mouse) were implanted to the flank of mice, and mice were sacrificed on day 25. Spleen was collected and IFN-gamma ELISPOT assay was performed using HER3 ECD and ICD peptide mix as stimulating antigens.

Heterologous prime-boost with mcDNA of pDNA followed by Ad-HER3 induced much stronger anti-HER3 cellular immune response based on ELISPOT assay (FIG. 3B). Especially, pDNA vaccine followed by Ad induced the most potent anti-HER3 response, stronger than mcDNA vaccine followed by Ad. The similar trend was confirmed in induced anti-HER3 humoral immune response (FIG. 4). pDNA vaccine followed by Ad induced the strongest antibody response against HER3 as shown in FIG. 4, and mcDNA vaccine followed by Ad showed similar or slightly less potent effect for anti-HER3 antibody generation. Seven days after the final vaccination, 4T1-HER3 cells were implanted to the flank of mice, and tumor sizes were monitored until humane endpoint. Mice were all euthanized on day 28 because some mice in Ad-GFP vaccine group reached humane endpoint. The average tumor volumes for each group are shown in FIG. 5. Compared to repeated Ad-HER3 vaccination, heterologous prime-boost vaccine with either mcDNA or plasmid DNA inhibited the tumor growth more significantly (FIG. 5). Because there was some discrepancy between the immunogenicity and antitumor effect for these different treatments, IFN-gamma ELISPOT assay was performed to determine the cellular immune response at the end of experiment (See FIG. 6). Interestingly, at the end of experiment, mcDNA vaccination group showed stronger anti-HER3 cellular immune response compared to pDNA, probably suggesting the longer persistence of antigen expression by mcDNA in vivo electroporation and thus longer lasting vaccine effect.

Comparison of pDNA/mcDNA/Ad Vector

As summarized in Table 3, female HER3 transgenic mice were vaccinated by intramuscular injection of plasmid DNA-hHER3/ECDC1C2 (25 µg/mouse), minicircle DNA-hHER3/ECDC1C2 (12.5 µg/mouse) or saline, followed by in vivo electroporation (50V, 5 pulses, pulse length 60 ms, interval time 200 ms). Electroporation was repeated twice to each mouse, placing the electrodes perpendicular from the $1^{st}$ position. Ad[E1]-hHER3 (2.6×10E10 vp/mouse) was injected into footpads, as a positive control. Three mice were included for each group. Two weeks after vaccination, mice were sacrificed and ELISPOT assay was performed. Each group has 3 mice.

TABLE 3

| Group | Number of Mouse | Vector | Schedule |
|---|---|---|---|
| 1 | 3 | saline | Day 0 |
| 2 | 3 | Ad[E1−]-HER3 | Day 0 |
| 3 | 3 | Plasmid DNA-hHER3/ECD-C1C2 | Day 0 |
| 4 | 3 | Minicircle DNA-hHER3/ECD-C1C2 | Day 0 |

Figure 8:
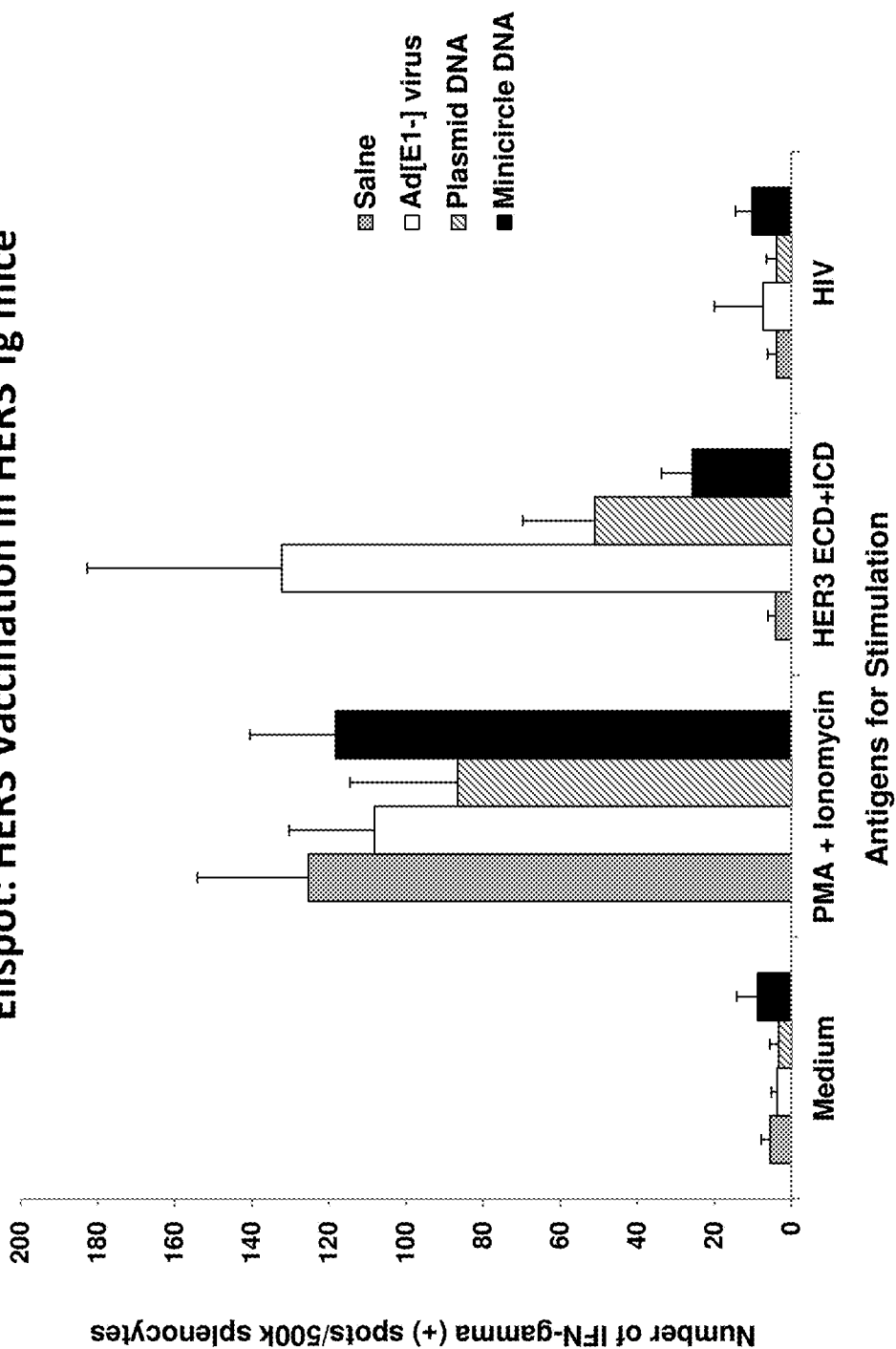
FIG. 8 shows the Cellular Immune Response induced in HER3 Transgenic Mice by Different Vaccine Strategies. Female HER3 transgenic mice were vaccinated by intramuscular injection of plasmid DNA-hHER3/ECDC1C2 (25 μg/mouse), minicircle DNA-hHER3/ECDC1C2 (12.5 μg/mouse) or saline, followed by in vivo electroporation (50V, 5 pulses, pulse length 60 ms, interval time 200 ms). Electroporation was repeated twice to each mouse, placing the electrodes perpendicular from the $1^{st}$ position. Ad[E1]-hHER3 (2.6×10E10 vp/mouse) was injected into footpads, as a positive control. Two weeks after vaccination, mice were sacrificed and ELISPOT assay was performed. Each group has 3 mice.
Figure 9:
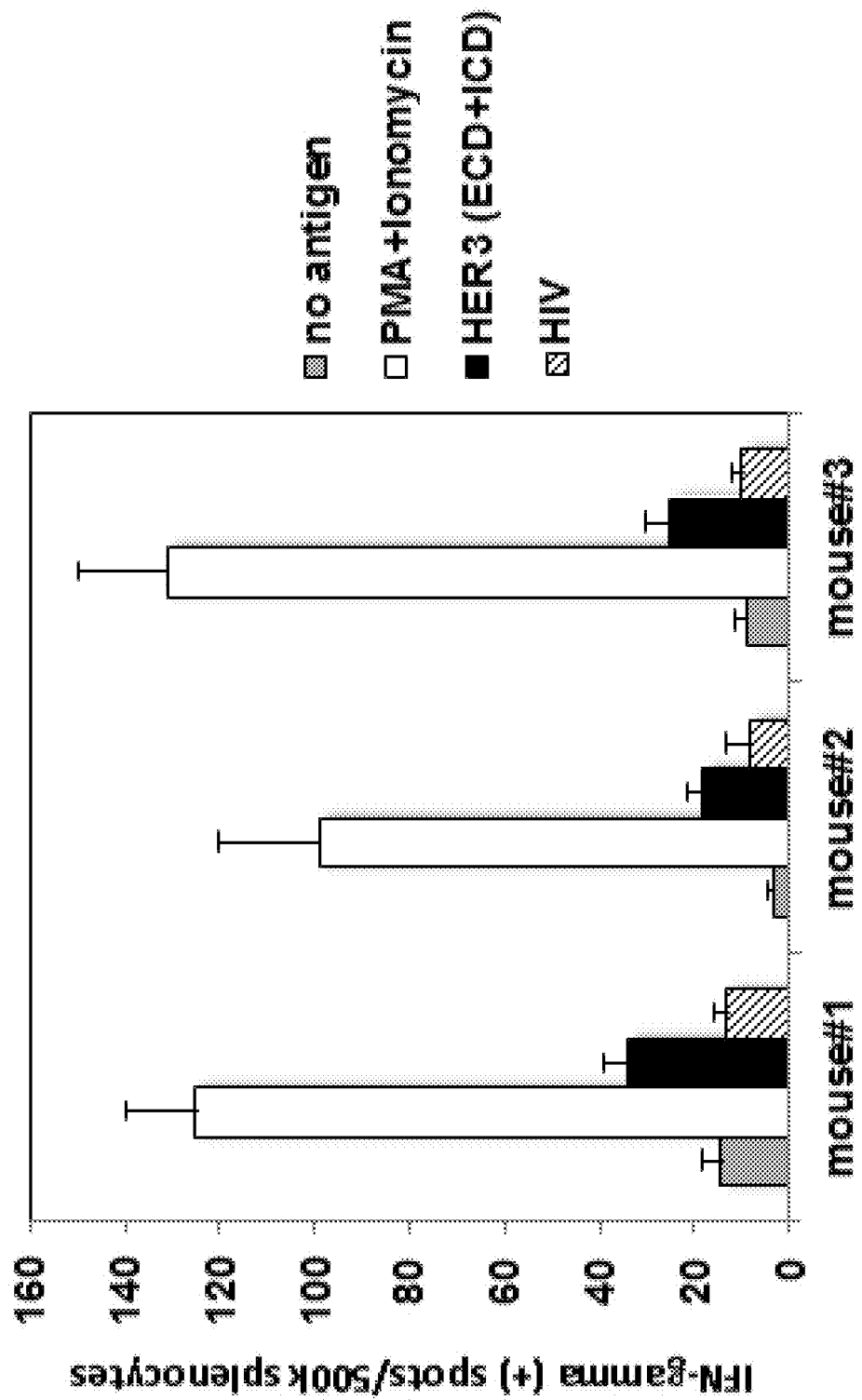
FIG. 9 shows the Cellular Immune Response induced in HER3 Transgenic Mice by Different Vaccine Strategies. Female HER3 transgenic mice were vaccinated by intramuscular injection of plasmid DNA-hHER3/ECDC1C2 (25 μg/mouse), minicircle DNA-hHER3/ECDC1C2 (12.5 μg/mouse) or saline, followed by in vivo electroporation (50V, 5 pulses, pulse length 60 ms, interval time 200 ms). Electroporation was repeated twice to each mouse, placing the electrodes perpendicular from the $1^{st}$ position. Ad[E1]-hHER3 (2.6×10E10 vp/mouse) was injected into footpads, as a positive control. Two weeks after vaccination, mice were sacrificed and ELISPOT assay was performed. Each group has 3 mice. Data of mice with minicircle DNA vaccine are shown.
Figure 10:
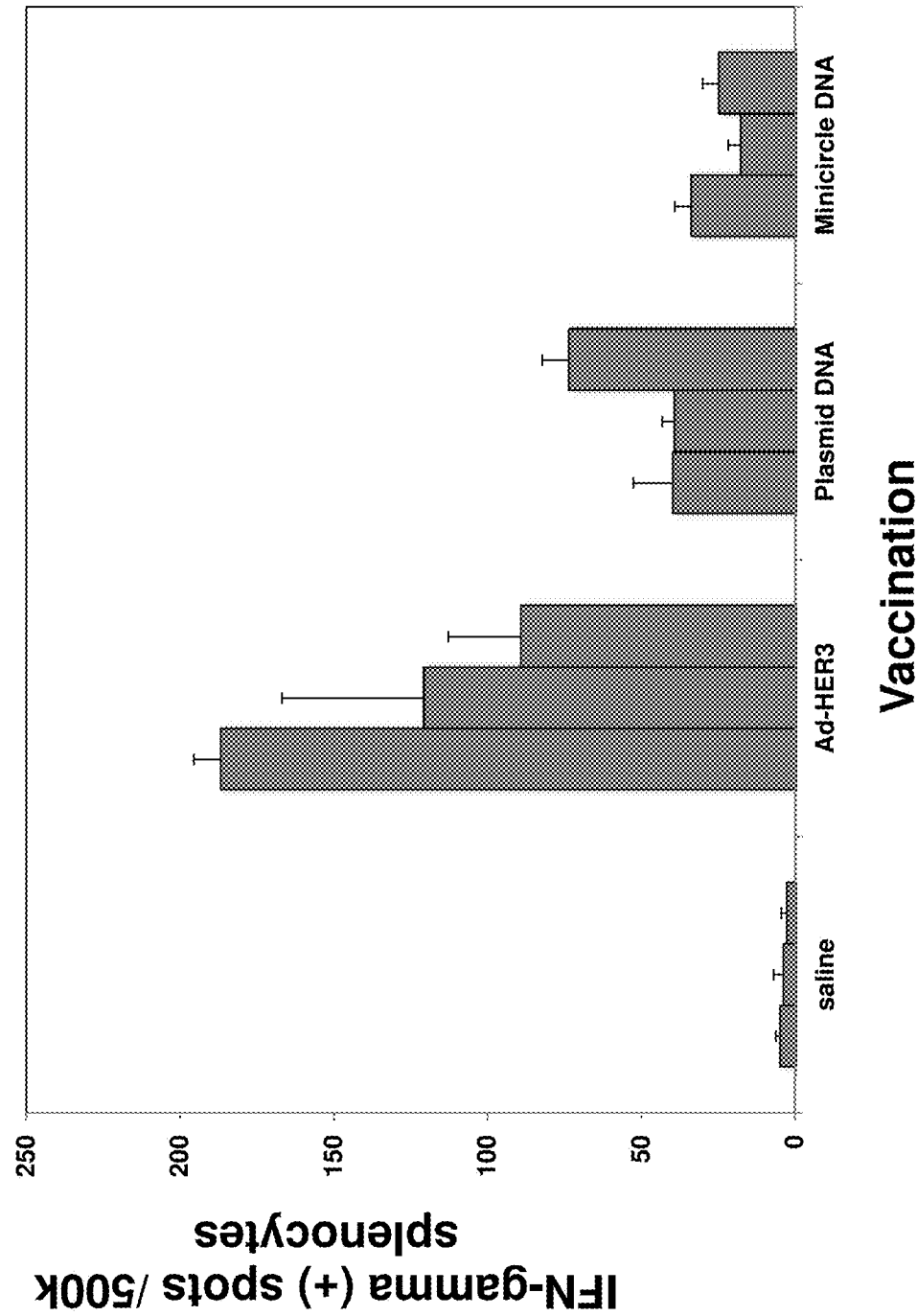
FIG. 10 shows the Cellular Immune Response induced in HER3 Transgenic Mice by Different Vaccine Strategies. Female HER3 transgenic mice were vaccinated by intramuscular injection of plasmid DNA-hHER3/ECDC1C2 (25 μg/mouse), minicircle DNA-hHER3/ECDC1C2 (12.5 μg/mouse) or saline, followed by in vivo electroporation (50V, 5 pulses, pulse length 60 ms, interval time 200 ms). Electroporation was repeated twice to each mouse, placing the electrodes perpendicular from the $1^{st}$ position. Ad[E1]-hHER3 (2.6×10E10 vp/mouse) was injected into footpads, as a positive control. Two weeks after vaccination, mice were sacrificed and ELISPOT assay was perfromed. Each group has 3 mice. Data for HER3 antigen (ECD+ICD peptide mix) are shown.

Minicircle DNA-hHER3/ECDC1C2 and plasmid DNA-hHER3/ECDC1C2 of equimolar amount were intramuscularly administered to mice, followed by in vivo electroporation. Both DNA vaccines induced HER3-specific cellular immune responses as shown by IFN-gamma ELISPOT assay (FIG. 8). There was no significant variation between mice in each DNA vaccine group (FIGS. 9 & 10), and stronger cellular response was observed in mice that received pDNA vaccine compared to mice that received mcDNA. Ad[E1]-hHER3 vaccine induced the strongest T cell response among these 3 vaccine strategies at least at 2 weeks time point after the single vaccination. Thus, to have comparable cellular immune response with Ad vaccine, higher dose or repeated vaccination of pDNA or mcDNA might be necessary. pDNA vaccine induced weaker to moderate anti-HER3 antibody level in mouse serum, while mcDNA did not induce detectable level of anti-HER3 antibody 2 weeks after vaccination (FIG. 11). pDNA vaccine and mcDNA vaccine may not induce strong antibody generation with relatively short time period (2 weeks), but may gradually increase the level of HER3 specific antibody generation.

Comparison of pDNA/mcDNA/Ad Vector Experiment 2

As summarized in Table 4, on day 0, Female HER3 transgenic mice were vaccinated by intramuscular injection of plasmid DNA-hHER3/ECDC1C2 (25 µg/mouse), minicircle DNA-hHER3/ECDC1C2 (25 µg/mouse) or saline, followed by in vivo electroporation (50V, 5 pulses, pulse length 60 ms, interval time 200 ms). Electroporation were repeated twice to each mouse, placing the electrodes perpendicular from the $1^{st}$ position. Ad[E1]-hHER3 (2.6× 10E10 vp/mouse) were injected into footpads, as a positive control. Two or 3 mice were included for each group. On day 14 (two weeks after priming vaccination), the same vaccinations were repeated to the mice. On day 21, a week after the boosting vaccine, mice were sacrificed and ELISPOT assay will be performed.

TABLE 4

| Group | Number of Mouse | Electro-poration | Vector | Schedule |
|---|---|---|---|---|
| 1 | 3 | + | saline | Days 0, 14 |
| 2 | 3 | − | Ad[E1−]-HER3 | Days 0, 14 |
| 3 | 3 | + | Plasmid DNA-hHER3/ECD-C1C2 | Days 0, 14 |
| 4 | 3 | + | Minicircle DNA-hHER3/ECD-C1C2 | Days 0, 14 |

Figure 12:
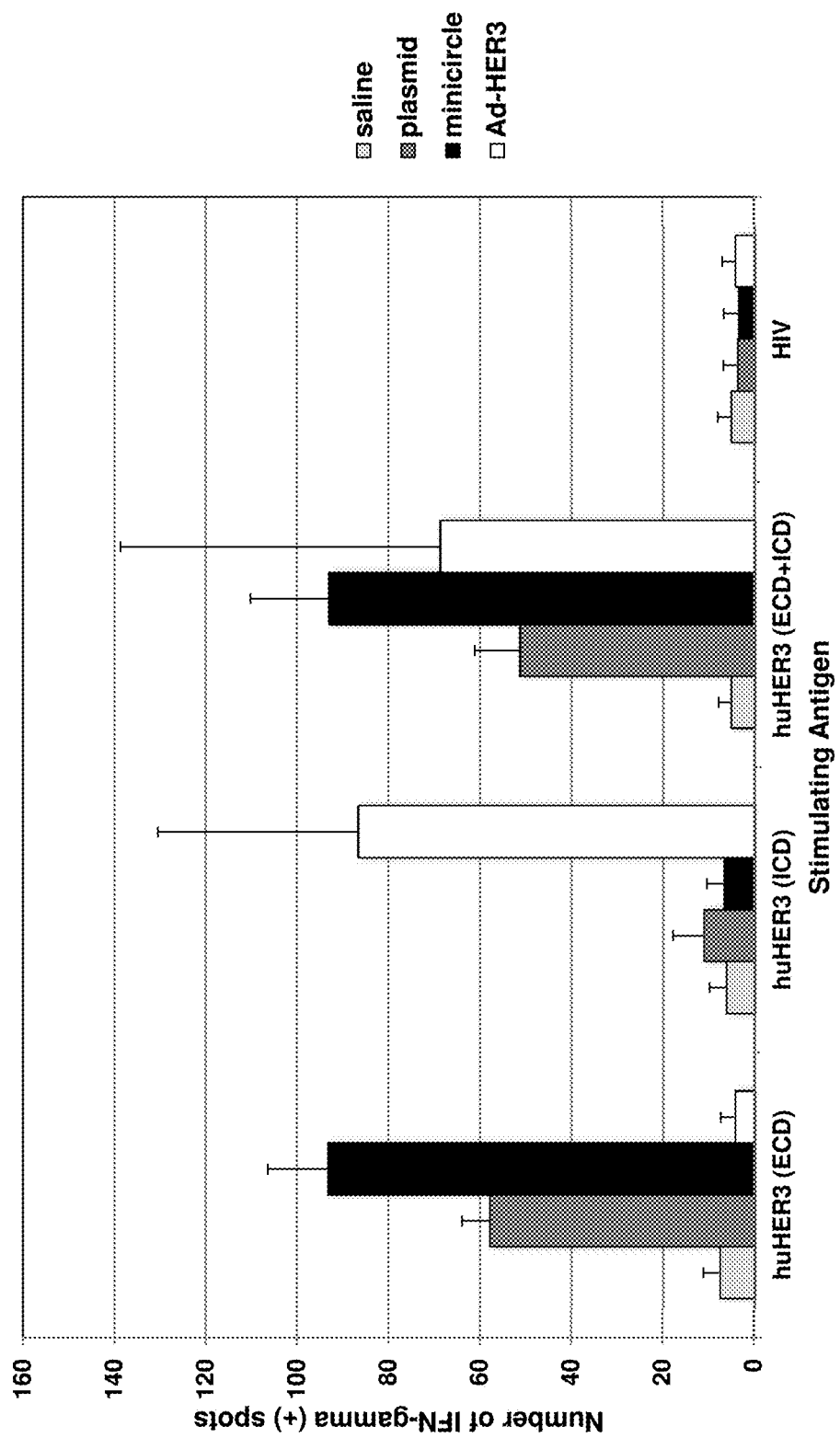
FIG. 12 shows IFN-gamma ELISPOT assay data. Mice were vaccinated twice with minicircle DNA (mcDNA-hHER3/ECD-mC1C2, 25 μg), plasmid DNA (pDNA-hHER3/ECD-mC1C2, 25 μg), or Adenoviral vector (Ad-hHER3, 2.6×10E10 vp) on days 0 and 14. On day 21, mice were euthanized and IFN-gamma ELISPOT assay was performed using splenocytes. HER3 peptide mix (ECD, ICD or ECD+ICD) or HIV peptide mix was used as stimulating antigens.
Figure 13:
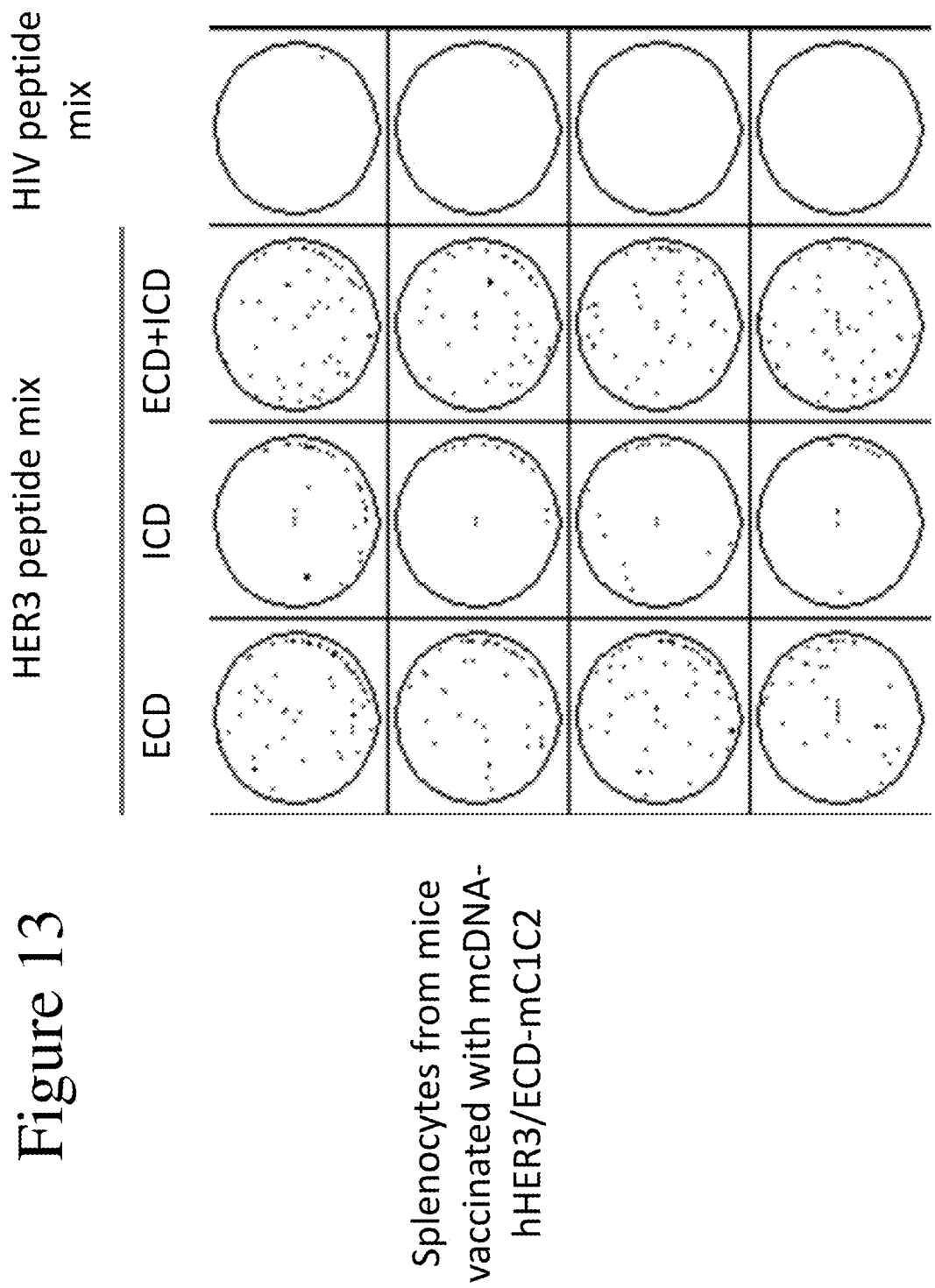
FIG. 13 shows IFN-gamma ELISPOT assay data. Mice were vaccinated twice with minicircle DNA (mcDNA-hHER3/ECD-mC1C2, 25 μg), plasmid DNA (pDNA-hHER3/ECD-mC1C2, 25 μg), or Adenoviral vector (Ad-hHER3, 2.6×10E10 vp) on days 0 and 14. On day 21, mice were euthanized and IFN-gamma ELISPOT assay was performed using splenocytes. HER3 peptide mix (ECD, ICD or ECD+ICD) or HIV peptide mix was used as stimulating antigens. Representative case of minicircle DNA (mcDNA-hHER3/ECD-C1C2) is shown.
Figure 14:
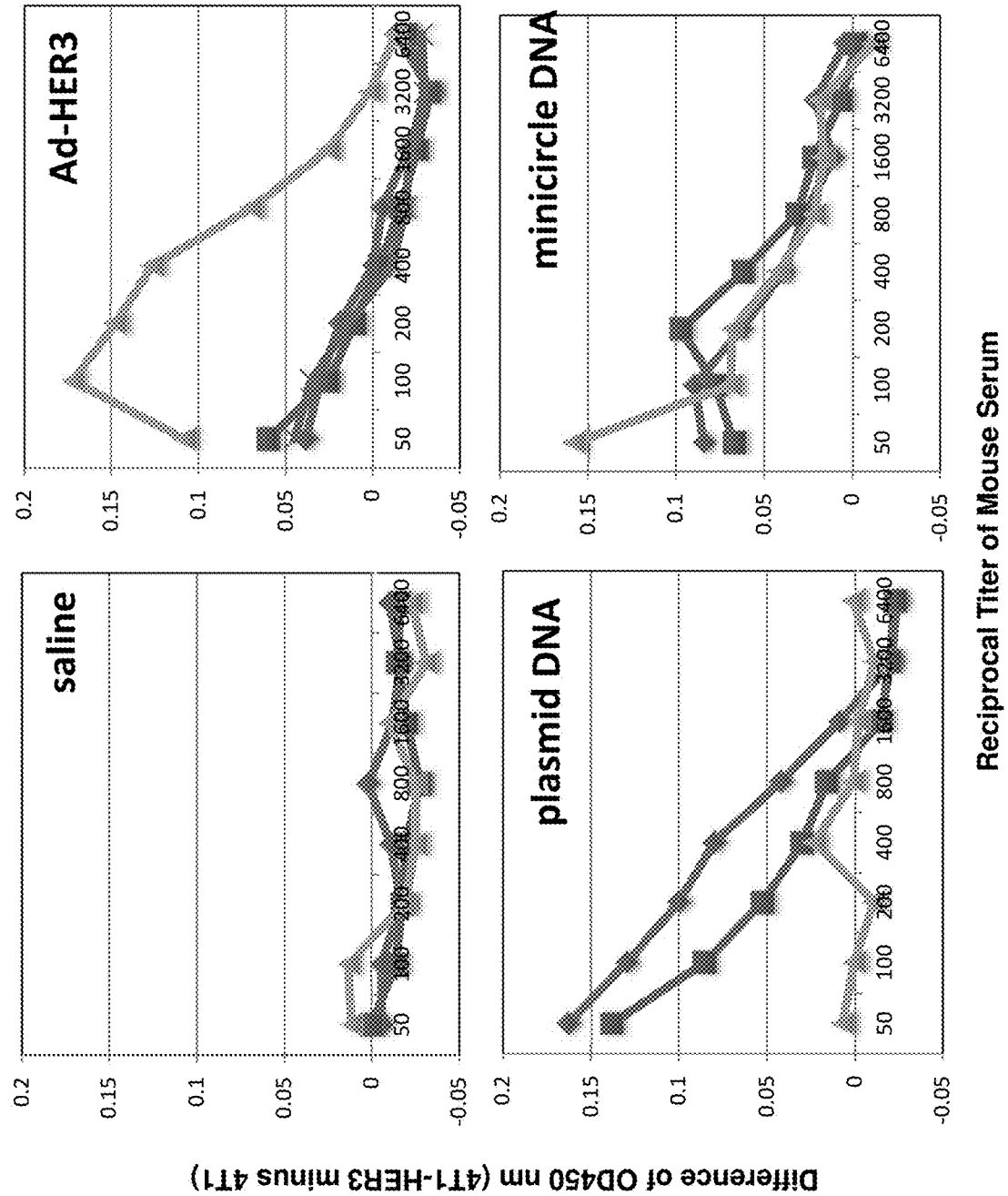
FIG. 14 shows cell-based ELISA data for anti-HER3 antibody. Mice were vaccinated twice with minicircle DNA (mcDNA-hHER3/ECD-mC1C2, 25 μg), plasmid DNA (pDNA-hHER3/ECD-mC1C2, 25 μg), or Adenoviral vector (Ad-hHER3, 2.6×10E10 vp) on days 0 and 14. On day 21, mice were euthanized and serum was collected. The level of anti-HER3 antibody was assessed by Cell-based ELISA using 4T1-HER3 cells and 4T1 cells. Titration of serum was made and added to the wells, follwed by HRP-conjugated 2ndary anti-mouse IgG antibody. Color was developed by TMB and plates were read at 450 nm after stopping reaction with $H_2SO_4$.

Based on the results of the IFN-gamma ELISPOT assay (FIG. 12), a stronger anti-HER3 cellular immune response was observed in mice vaccinated twice with minicircle DNA-hHER3/ECDC1C2 compared to mice vaccinated twice with plasmid DNA-hHER3/ECDC1C2 when equal amount of DNA was applied. As expected, the response was seen only for extracellular domain, but not for intracellular domain. FIG. 13 shows the representative case of ELISPOT assay, where the IFN-gamma positive spots were developed with the splenocytes from the mice vaccinated with minicircle DNA-hHER3/ECDC1C2. As stimulating antigens, ECD, ICD or ECD plus ICD of HERS protein were used, and HIV peptide mix was used as a negative control. Importantly, in contrast with the comparison experiment 1 (FIGS. 8-10) where vaccination was given to mice only once before immune assays, repeated vaccination with mcDNA was more potent to induce antigen-specific cellular immune response than repeated pDNA vaccines, probably because of the longer persistence of antigen expression by mcDNA in vivo electroporation and thus longer lasting vaccine effect. In addition, as shown in ELISPOT assay, repeated Ad[E1]-hHER3 vaccines no longer had stronger anti-HER3 cellular response over mcDNA or pDNA vaccine, probably because of neutralization effect by anti-Ad antibody generated after the $1^{st}$ vaccination. Based on the results of Cell-based ELISA to detect anti-HER3 antibody level in mice, mcDNA and pDNA showed similar effect for anti-HER3 antibody generation (FIG. 14). Therefore, it was suggested that repeated vaccination with mcDNA vaccines is more potent in inducing antigen-specific T cell response than repeated pDNA vaccines, while both vaccination strategies have similar potencies to induce humoral immune response.

REFERENCES

1. Delcayre A, Estelles A, Sperinde J, Roulon T, Paz P, Aguilar B, Villanueva J, Khine S, and Le Pecq J B. Exosome Display technology: applications to the development of new diagnostics and therapeutics. *Blood cells, molecules & diseases*. 2005; 35(2):158-68.
2. Tiriveedhi V, Tucker N, Herndon J, Li L, Sturmoski M, Ellis M, Ma C, Naughton M, Lockhart A C, Gao F, et al. Safety and preliminary evidence of biologic efficacy of a mammaglobin-a DNA vaccine in patients with stable metastatic breast cancer. *Clinical cancer research: an official journal of the American Association for Cancer Research*. 2014; 20(23):5964-75.

We claim:

1. A method of treating a HER3-expressing cancer or precancer or of reducing the likelihood of the cancer developing resistance to a cancer therapeutic or prevention agent in a subject comprising:
   a) administering to the subject a therapeutically effective amount of a first dose of a minicircle DNA comprising first polynucleotide encoding an antigenic polypeptide comprising the extracellular domain of HER3 (amino acids 1-643 of SEQ ID NO: 2), wherein the first polynucleotide is circular and lacks a bacterial origin of replication and an antibiotic resistance gene;
   b) administering to the subject a therapeutically effective amount of a second dose of the minicircle DNA; and
   c) subsequently administering to the subject a therapeutically effective amount of an adenoviral vaccine vector encoding the antigenic polypeptide;
   wherein the method produces an extended anti-HER3 cellular immune response.

2. The method of claim 1, wherein the minicircle DNA comprises a polynucleotide construct comprising a heterologous promoter operably connected to a first polynucleotide encoding the extracellular domain of HER3 fused to the C1C2 domains of lactadherin comprising SEQ ID NO:12.

3. The method of claim 1, wherein steps a)-c) are performed before administration of the cancer therapeutic or prevention agent.

4. The method of claim 1, wherein the cancer therapeutic or prevention agent is an agent targeting HER2, HER1, estrogen receptor, EGFR, or IGF1R.

5. The method of claim 1, further comprising administering a checkpoint inhibitor immunomodulatory agent and wherein the DNA vaccine and the vaccine vector composition are administered concurrently with, before or after administration of the checkpoint inhibitor immunomodulatory agent.

6. The method of claim 1, wherein the cancer or precancer is selected from a breast, prostate, lung, ovarian, colon, rectal, pancreas, bladder, head and neck or liver cancer or precancer.

7. The method of claim 1, wherein the subject is human.

* * * * *

SEQUENCE LISTING

<160> NUMBER OF SEQ ID NOS: 44

<210> SEQ ID NO 1
<211> LENGTH: 331
<212> TYPE: PRT
<213> ORGANISM: Homo sapiens
<220> FEATURE:
<221> NAME/KEY: misc_feature
<222> LOCATION: (1)..(331)
<223> OTHER INFORMATION: Human HER3 Protein amino acid sequence

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

```
Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 2
<211> LENGTH: 1342
<212> TYPE: PRT
<213> ORGANISM: Homo sapiens
<220> FEATURE:
<221> NAME/KEY: misc_feature
<222> LOCATION: (1)..(1342)
<223> OTHER INFORMATION: Human HER3 Protein Precursor amino acid
      sequence

<400> SEQUENCE: 2

Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
             20                  25                  30

Leu Asn Gly Leu Ser Val Thr Gly Asp Ala Glu Asn Gln Tyr Gln Thr
            35                  40                  45
```

```
Leu Tyr Lys Leu Tyr Glu Arg Cys Glu Val Val Met Gly Asn Leu Glu
         50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
        130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
450                 455                 460
```

-continued

His His Ser Leu Asn Trp Thr Lys Val Leu Arg Gly Pro Thr Glu Glu
465                 470                 475                 480

Arg Leu Asp Ile Lys His Asn Arg Pro Arg Asp Cys Val Ala Glu
        485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
        580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
            805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
        850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser

```
                    885                 890                 895
Tyr Gly Val Thr Val Trp Glu Leu Met Thr Phe Gly Ala Glu Pro Tyr
                900                 905                 910
Ala Gly Leu Arg Leu Ala Glu Val Pro Asp Leu Leu Glu Lys Gly Glu
            915                 920                 925
Arg Leu Ala Gln Pro Gln Ile Cys Thr Ile Asp Val Tyr Met Val Met
        930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
            980                 985                 990
His Gly Leu Thr Asn Lys Lys Leu Glu Glu Val Glu Leu Glu Pro Glu
        995                 1000                1005
Leu Asp Leu Asp Leu Asp Leu Glu Ala Glu Glu Asp Asn Leu Ala
    1010            1015            1020
Thr Thr Thr Leu Gly Ser Ala Leu Ser Leu Pro Val Gly Thr Leu
    1025            1030            1035
Asn Arg Pro Arg Gly Ser Gln Ser Leu Leu Ser Pro Ser Ser Gly
    1040            1045            1050
Tyr Met Pro Met Asn Gln Gly Asn Leu Gly Gly Ser Cys Gln Glu
    1055            1060            1065
Ser Ala Val Ser Gly Ser Ser Glu Arg Cys Pro Arg Pro Val Ser
    1070            1075            1080
Leu His Pro Met Pro Arg Gly Cys Leu Ala Ser Glu Ser Ser Glu
    1085            1090            1095
Gly His Val Thr Gly Ser Glu Ala Glu Leu Gln Glu Lys Val Ser
    1100            1105            1110
Met Cys Arg Ser Arg Ser Arg Ser Arg Ser Pro Arg Pro Arg Gly
    1115            1120            1125
Asp Ser Ala Tyr His Ser Gln Arg His Ser Leu Leu Thr Pro Val
    1130            1135            1140
Thr Pro Leu Ser Pro Pro Gly Leu Glu Glu Glu Asp Val Asn Gly
    1145            1150            1155
Tyr Val Met Pro Asp Thr His Leu Lys Gly Thr Pro Ser Ser Arg
    1160            1165            1170
Glu Gly Thr Leu Ser Ser Val Gly Leu Ser Ser Val Leu Gly Thr
    1175            1180            1185
Glu Glu Glu Asp Glu Asp Glu Glu Tyr Glu Tyr Met Asn Arg Arg
    1190            1195            1200
Arg Arg His Ser Pro Pro His Pro Pro Arg Pro Ser Ser Leu Glu
    1205            1210            1215
Glu Leu Gly Tyr Glu Tyr Met Asp Val Gly Ser Asp Leu Ser Ala
    1220            1225            1230
Ser Leu Gly Ser Thr Gln Ser Cys Pro Leu His Pro Val Pro Ile
    1235            1240            1245
Met Pro Thr Ala Gly Thr Thr Pro Asp Glu Asp Tyr Glu Tyr Met
    1250            1255            1260
Asn Arg Gln Arg Asp Gly Gly Gly Pro Gly Gly Asp Tyr Ala Ala
    1265            1270            1275
Met Gly Ala Cys Pro Ala Ser Glu Gln Gly Tyr Glu Glu Met Arg
    1280            1285            1290
```

```
Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 3
<211> LENGTH: 1239
<212> TYPE: PRT
<213> ORGANISM: Homo sapiens
<220> FEATURE:
<221> NAME/KEY: misc_feature
<222> LOCATION: (1)..(1239)
<223> OTHER INFORMATION: Homo sapiens HER2 polypeptide

<400> SEQUENCE: 3

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285
```

-continued

```
Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Val Ser
625                 630                 635                 640

Ala Val Val Gly Ile Leu Leu Val Val Leu Gly Val Val Phe Gly
                645                 650                 655

Ile Leu Ile Lys Arg Arg Gln Gln Lys Ile Arg Lys Tyr Thr Met Arg
                660                 665                 670

Arg Leu Leu Gln Glu Thr Glu Leu Val Glu Pro Leu Thr Pro Ser Gly
            675                 680                 685

Ala Met Pro Asn Gln Ala Gln Met Arg Ile Leu Lys Glu Thr Glu Leu
    690                 695                 700

Arg Lys Val Lys Val Leu Gly Ser Gly Ala Phe Gly Thr Val Tyr Lys
```

-continued

```
            705                 710                 715                 720
        Gly Ile Trp Ile Pro Asp Gly Glu Asn Val Lys Ile Pro Val Ala Ile
                        725                 730                 735
        Lys Val Leu Arg Glu Asn Thr Ser Pro Lys Ala Asn Lys Glu Ile Leu
                        740                 745                 750
        Asp Glu Ala Tyr Val Met Ala Gly Val Gly Ser Pro Tyr Val Ser Arg
                        755                 760                 765
        Leu Leu Gly Ile Cys Leu Thr Ser Thr Val Gln Leu Val Thr Gln Leu
                        770                 775                 780
        Met Pro Tyr Gly Cys Leu Leu Asp His Val Arg Glu Asn Arg Gly Arg
        785                 790                 795                 800
        Leu Gly Ser Gln Asp Leu Leu Asn Trp Cys Met Gln Ile Ala Lys Gly
                        805                 810                 815
        Met Ser Tyr Leu Glu Asp Val Arg Leu Val His Arg Asp Leu Ala Ala
                        820                 825                 830
        Arg Asn Val Leu Val Lys Ser Pro Asn His Val Lys Ile Thr Asp Phe
                        835                 840                 845
        Gly Leu Ala Arg Leu Leu Asp Ile Asp Glu Thr Glu Tyr His Ala Asp
                        850                 855                 860
        Gly Gly Lys Val Pro Ile Lys Trp Met Ala Leu Glu Ser Ile Leu Arg
        865                 870                 875                 880
        Arg Arg Phe Thr His Gln Ser Asp Val Trp Ser Tyr Gly Val Thr Val
                        885                 890                 895
        Trp Glu Leu Met Thr Phe Gly Ala Lys Pro Tyr Asp Gly Ile Pro Ala
                        900                 905                 910
        Arg Glu Ile Pro Asp Leu Leu Glu Lys Gly Glu Arg Leu Pro Gln Pro
                        915                 920                 925
        Pro Ile Cys Thr Ile Asp Val Tyr Met Ile Met Val Lys Cys Trp Met
                        930                 935                 940
        Ile Asp Ser Glu Cys Arg Pro Arg Phe Arg Glu Leu Val Ser Glu Phe
        945                 950                 955                 960
        Ser Arg Met Ala Arg Asp Pro Gln Arg Phe Val Val Ile Gln Asn Glu
                        965                 970                 975
        Asp Leu Gly Pro Ala Ser Pro Leu Asp Ser Thr Phe Tyr Arg Ser Leu
                        980                 985                 990
        Leu Glu Asp Asp Asp Met Gly Asp Leu Val Asp Ala Glu Glu Tyr Leu
                        995                 1000                1005
        Val Pro Gln Gln Gly Phe Phe Cys Pro Asp Pro Ala Pro Gly Ala
                        1010                1015                1020
        Gly Gly Met Val His His Arg His Arg Ser Ser Thr Arg Ser
                        1025                1030                1035
        Gly Gly Gly Asp Leu Thr Leu Gly Leu Glu Pro Ser Glu Glu Glu
                        1040                1045                1050
        Ala Pro Arg Ser Pro Leu Ala Pro Ser Glu Gly Ala Gly Ser Asp
                        1055                1060                1065
        Val Phe Asp Gly Asp Leu Gly Met Gly Ala Ala Lys Gly Leu Gln
                        1070                1075                1080
        Ser Leu Pro Thr His Asp Pro Ser Pro Leu Gln Arg Tyr Ser Glu
                        1085                1090                1095
        Asp Pro Thr Val Pro Leu Pro Ser Glu Thr Asp Gly Tyr Val Ala
                        1100                1105                1110
        Pro Leu Thr Cys Ser Pro Gln Pro Glu Tyr Val Asn Gln Pro Asp
                        1115                1120                1125
```

```
Val Arg Pro Gln Pro Pro Ser Pro Arg Glu Gly Pro Leu Pro Ala
    1130                1135                1140

Ala Arg Pro Ala Gly Ala Thr Leu Glu Arg Ala Lys Thr Leu Ser
    1145                1150                1155

Pro Gly Lys Asn Gly Val Val Lys Asp Val Phe Ala Phe Gly Gly
    1160                1165                1170

Ala Val Glu Asn Pro Glu Tyr Leu Thr Pro Gln Gly Gly Ala Ala
    1175                1180                1185

Pro Gln Pro His Pro Pro Ala Phe Ser Pro Ala Phe Asp Asn
    1190                1195                1200

Leu Tyr Tyr Trp Asp Gln Asp Pro Pro Glu Arg Gly Ala Pro Pro
    1205                1210                1215

Ser Thr Phe Lys Gly Thr Pro Thr Ala Glu Asn Pro Glu Tyr Leu
    1220                1225                1230

Gly Leu Asp Val Pro Val
    1235
```

<210> SEQ ID NO 4
<211> LENGTH: 111
<212> TYPE: PRT
<213> ORGANISM: Homo sapiens
<220> FEATURE:
<221> NAME/KEY: misc_feature
<222> LOCATION: (1)..(111)
<223> OTHER INFORMATION: Homo sapiens HER2 polypeptide

<400> SEQUENCE: 4

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn
            100                 105                 110
```

<210> SEQ ID NO 5
<211> LENGTH: 668
<212> TYPE: PRT
<213> ORGANISM: Homo sapiens
<220> FEATURE:
<221> NAME/KEY: misc_feature
<222> LOCATION: (1)..(668)
<223> OTHER INFORMATION: Homo sapiens HER2 polypeptide

<400> SEQUENCE: 5

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45
```

```
Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
                115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
```

```
                     465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Pro Leu Thr Ser Ile Val Ser
625                 630                 635                 640

Ala Val Val Gly Ile Leu Leu Val Val Val Leu Gly Val Val Phe Gly
                645                 650                 655

Ile Leu Ile Lys Arg Arg Gln Gln Lys Ile Arg Lys
                660                 665

<210> SEQ ID NO 6
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens ESR1 polypeptide

<400> SEQUENCE: 6

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
                130                 135                 140

Gly Pro Pro Ala Phe Tyr Arg Pro Asn Ser Asp Asn Arg Arg Gln Gly
145                 150                 155                 160
```

```
Gly Arg Glu Arg Leu Ala Ser Thr Asn Asp Lys Gly Ser Met Ala Met
            165                 170                 175

Glu Ser Ala Lys Glu Thr Arg Tyr Cys Ala Val Cys Asn Asp Tyr Ala
        180                 185                 190

Ser Gly Tyr His Tyr Gly Val Trp Ser Cys Glu Gly Cys Lys Ala Phe
    195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Asn Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575
```

His Ser Leu Gln Lys Tyr Tyr Ile Thr Gly Glu Ala Glu Gly Phe Pro
            580                 585                 590

Ala Thr Val
        595

<210> SEQ ID NO 7
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens ESR1 polypeptide

<400> SEQUENCE: 7

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro

```
                        325                 330                 335
        Phe Ser Glu Ala Ser Met Met Gly Leu Leu Thr Asn Leu Ala Asp Arg
                    340                 345                 350

Glu Leu Val His Met Ile Asn Trp Ala Lys Arg Val Pro Gly Phe Val
                    355                 360                 365

Asp Leu Thr Leu His Asp Gln Val His Leu Leu Glu Cys Ala Trp Leu
                370                 375                 380

Glu Ile Leu Met Ile Gly Leu Val Trp Arg Ser Met Glu His Pro Gly
        385                 390                 395                 400

Lys Leu Leu Phe Ala Pro Asn Leu Leu Asp Arg Asn Gln Gly Lys
                        405                 410                 415

Cys Val Glu Gly Met Val Glu Ile Phe Asp Met Leu Leu Ala Thr Ser
                    420                 425                 430

Ser Arg Phe Arg Met Met Asn Leu Gln Gly Glu Glu Phe Val Cys Leu
                    435                 440                 445

Lys Ser Ile Ile Leu Leu Asn Ser Gly Val Tyr Thr Phe Leu Ser Ser
                    450                 455                 460

Thr Leu Lys Ser Leu Glu Glu Lys Asp His Ile His Arg Val Leu Asp
        465                 470                 475                 480

Lys Ile Thr Asp Thr Leu Ile His Leu Met Ala Lys Ala Gly Leu Thr
                        485                 490                 495

Leu Gln Gln Gln His Gln Arg Leu Ala Gln Leu Leu Leu Ile Leu Ser
                    500                 505                 510

His Ile Arg His Met Ser Asn Lys Gly Met Glu His Leu Tyr Ser Met
                    515                 520                 525

Lys Cys Lys Asn Val Val Pro Leu Ser Asp Leu Leu Leu Glu Met Leu
                530                 535                 540

Asp Ala His Arg Leu His Ala Pro Thr Ser Arg Gly Gly Ala Ser Val
        545                 550                 555                 560

Glu Glu Thr Asp Gln Ser His Leu Ala Thr Ala Gly Ser Thr Ser Ser
                        565                 570                 575

His Ser Leu Gln Lys Tyr Tyr Ile Thr Gly Glu Ala Glu Gly Phe Pro
                    580                 585                 590

Ala Thr Val
                595

<210> SEQ ID NO 8
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens ESR1 polypeptide

<400> SEQUENCE: 8

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80
```

```
Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495
```

```
Leu Gln Gln Gln His Gln Arg Leu Ala Gln Leu Leu Ile Leu Ser
                500                 505                 510

His Ile Arg His Met Ser Asn Lys Gly Met Glu His Leu Tyr Ser Met
            515                 520                 525

Lys Cys Lys Asn Val Val Pro Leu Tyr Gly Leu Leu Leu Glu Met Leu
        530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 9
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens ESR1 polypeptide

<400> SEQUENCE: 9

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
```

```
                245                 250                 255
Lys Asp Arg Arg Gly Arg Met Leu Lys His Lys Arg Gln Arg Asp
            260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Arg Asn
            290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 10
<211> LENGTH: 315
<212> TYPE: PRT
<213> ORGANISM: Homo sapiens
<220> FEATURE:
<221> NAME/KEY: misc_feature
<222> LOCATION: (1)..(315)
<223> OTHER INFORMATION: Lactadherin C1C2

<400> SEQUENCE: 10
```

```
Ser Thr Gln Leu Gly Met Glu Gly Gly Ala Ile Ala Asp Ser Gln Ile
1               5                   10                  15

Ser Ala Ser Ser Val Tyr Met Gly Phe Met Gly Leu Gln Arg Trp Gly
            20                  25                  30

Pro Glu Leu Ala Arg Leu Tyr Arg Thr Gly Ile Val Asn Ala Trp Thr
            35                  40                  45

Ala Ser Asn Tyr Asp Ser Lys Pro Trp Ile Gln Val Asn Leu Leu Arg
        50                  55                  60

Lys Met Arg Val Ser Gly Val Met Thr Gln Gly Ala Ser Arg Ala Gly
65                  70                  75                  80

Arg Ala Glu Tyr Leu Lys Thr Phe Lys Val Ala Tyr Ser Leu Asp Gly
                85                  90                  95

Arg Lys Phe Glu Phe Ile Gln Asp Glu Ser Gly Gly Asp Lys Glu Phe
            100                 105                 110

Leu Gly Asn Leu Asp Asn Asn Ser Leu Lys Val Asn Met Phe Asn Pro
        115                 120                 125

Thr Leu Glu Ala Gln Tyr Ile Lys Leu Tyr Pro Val Ser Cys His Arg
    130                 135                 140

Gly Cys Thr Leu Arg Phe Glu Leu Leu Gly Cys Glu Leu His Gly Cys
145                 150                 155                 160

Ser Glu Pro Leu Gly Leu Lys Asn Asn Thr Ile Pro Asp Ser Gln Met
                165                 170                 175

Ser Ala Ser Ser Ser Tyr Lys Thr Trp Asn Leu Arg Ala Phe Gly Trp
            180                 185                 190

Tyr Pro His Leu Gly Arg Leu Asp Asn Gln Gly Lys Ile Asn Ala Trp
        195                 200                 205

Thr Ala Gln Ser Asn Ser Ala Lys Glu Trp Leu Gln Val Asp Leu Gly
    210                 215                 220

Thr Gln Arg Gln Val Thr Gly Ile Ile Thr Gln Gly Ala Arg Asp Phe
225                 230                 235                 240

Gly His Ile Gln Tyr Val Ala Ser Tyr Lys Val Ala His Ser Asp Asp
                245                 250                 255

Gly Val Gln Trp Thr Val Tyr Glu Glu Gln Gly Ser Ser Lys Val Phe
            260                 265                 270

Gln Gly Asn Leu Asp Asn Asn Ser His Lys Lys Asn Ile Phe Glu Lys
        275                 280                 285

Pro Phe Met Ala Arg Tyr Val Arg Val Leu Pro Val Ser Trp His Asn
    290                 295                 300

Arg Ile Thr Leu Arg Leu Glu Leu Leu Gly Cys
305                 310                 315

<210> SEQ ID NO 11
<211> LENGTH: 2880
<212> TYPE: DNA
<213> ORGANISM: Homo sapiens
<220> FEATURE:
<221> NAME/KEY: misc_feature
<222> LOCATION: (1)..(2880)
<223> OTHER INFORMATION: DNA sequence of Human Her3ECDC1C2

<400> SEQUENCE: 11
accatgaggg cgaacgacgc tctgcaggtg ctgggcttgc ttttcagcct ggcccggggc      60
tccgaggtgg gcaactctca ggcagtgtgt cctgggactc tgaatggcct gagtgtgacc     120
ggcgatgctg agaaccaata ccagacactg tacaagctct acgagaggtg tgaggtggtg     180
```

-continued

```
atggggaacc ttgagattgt gctcacggga cacaatgccg acctctcctt cctgcagtgg    240
attcgagaag tgacaggcta tgtcctcgtg gccatgaatg aattctctac tctaccattg    300
cccaacctcc gcgtggtgcg agggacccag gtctacgatg ggaagtttgc catcttcgtc    360
atgttgaact ataacaccaa ctccagccac gctctgcgcc agctccgctt gactcagctc    420
accgagattc tgtcaggggg tgtttatatt gagaagaacg ataagctttg tcacatggac    480
acaattgact ggagggacat cgtgagggac cgagatgctg agatagtggt gaaggacaat    540
ggcagaagct gtcccccctg tcatgaggtt tgcaaggggc gatgctgggg tcctggatca    600
gaagactgcc agacattgac caagaccatc tgtgctcctc agtgtaatgg tcactgcttt    660
gggcccaacc ccaaccagtg ctgccatgat gagtgtgccg ggggctgctc aggccctcag    720
gacacagact gctttgcctg ccggcacttc aatgacagtg gagcctgtgt acctcgctgt    780
ccacagcctc ttgtctacaa caagctaact ttccagctgg aacccaatcc ccacaccaag    840
tatcagtatg gaggagtttg tgtagccagc tgtccccata actttgtggt ggatcaaaca    900
tcctgtgtca gggcctgtcc tcctgacaag atggaagtag ataaaaatgg gctcaagatg    960
tgtgagcctt gtggggact atgtcccaaa gcctgtgagg gaacaggctc tgggagccgc   1020
ttccagactg tggactcgag caacattgat ggatttgtga actgcaccaa gatcctgggc   1080
aacctggact ttctgatcac cggcctcaat ggagacccct ggcacaagat ccctgccctg   1140
gacccagaga agctcaatgt cttccggaca gtacgggaga tcacaggtta cctgaacatc   1200
cagtcctggc cgccccacat gcacaacttc agtgttttt ccaatttgac aaccattgga   1260
ggcagaagcc tctacaaccg ggcttctca ttgttgatca tgaagaactt gaatgtcaca   1320
tctctgggct tccgatccct gaaggaaatt agtgctgggc gtatctatat aagtgccaat   1380
aggcagctct gctaccacca ctcttttgaac tggaccaagg tgcttcgggg gcctacggaa   1440
gagcgactag acatcaagca taatcggccg cgcagagact gcgtggcaga gggcaaagtg   1500
tgtgacccac tgtgctcctc tggggggatgc tggggcccag gcctggtca gtgcttgtcc   1560 tgtcgaaatt atagccgagg aggtgtctgt gtgacccact gcaactttct gaatggggag   1620
cctcgagaat tgcccatga ggccgaatgc ttctcctgcc acccggaatg ccaacccatg   1680
gagggcactg ccacatgcaa tggctcgggc tctgatactt gtgctcaatg tgcccatttt   1740
cgagatgggc cccactgtgt gagcagctgc cccatggag tcctaggtgc aagggccca   1800 atctacaagt acccagatgt tcagaatgaa tgtcggccct gccatgagaa ctgcacccag   1860
gggtgtaaag gaccagagct tcaagactgt ttaggacaaa cactggtgct gatcggcaaa   1920
acccatctga catctacaca gctgggcatg aaggggcgc ccattgctga ttcacagatt   1980
tccgcctcgt ctgtgtatat gggtttcatg ggcttcagc gctggggccc ggagctggct   2040
cgtctgtacc gcacagggat cgtcaatgcc tggacagcca gcaactatga tagcaagccc   2100
tggatccagg tgaaccttct gcggaagatg cgggtatcag gtgtgatgac gcagggtgcc   2160
agccgtgccg ggagggcgga gtacctgaag accttcaagg tggcttacag cctcgacgga   2220
cgcaagtttg agttcatcca ggatgaaagc ggtggagaca aggagttttt gggtaacctg   2280
gacaacaaca gcctgaaggt taacatgttc aacccgactc tggaggcaca gtacataaag   2340
ctgtaccctg tttcgtgcca ccgcggctgc acccctcgct tcgagctcct gggctgtgag   2400
ttgcacggat gttctgagcc cctgggcctg aagaataaca caattcctga cagccagatg   2460
tcagcctcca gcagctacaa gacatggaac ctgcgtgctt ttggctggta cccccacttg   2520
ggaaggctgg ataatcaggg caagatcaat gcctggacgg ctcagagcaa cagtgccaag   2580
```

```
gaatggctgc aggttgacct gggcactcag aggcaagtga caggaatcat cacccagggg    2640
gcccgtgact ttggccacat ccagtatgtg gcgtcctaca aggtagccca cagtgatgat    2700
ggtgtgcagt ggactgtata tgaggagcaa ggaagcagca aggtcttcca gggcaacttg    2760
gacaacaact cccacaagaa gaacatcttc gagaaaccct tcatggctcg ctacgtgcgt    2820
gtccttccag tgtcctggca taaccgcatc accctgcgcc tggagctgct gggctgttaa    2880
```

<210> SEQ ID NO 12
<211> LENGTH: 958
<212> TYPE: PRT
<213> ORGANISM: Homo sapiens
<220> FEATURE:
<221> NAME/KEY: misc_feature
<222> LOCATION: (1)..(958)
<223> OTHER INFORMATION: HER3C1C2-lactadherin protein (polypeptide)
      sequence

<400> SEQUENCE: 12

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
```

-continued

```
            290                 295                 300
Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Ser Thr Gln Leu Gly Met Glu Gly Gly Ala Ile Ala Asp
            645                 650                 655

Ser Gln Ile Ser Ala Ser Ser Val Tyr Met Gly Phe Met Gly Leu Gln
            660                 665                 670

Arg Trp Gly Pro Glu Leu Ala Arg Leu Tyr Arg Thr Gly Ile Val Asn
            675                 680                 685

Ala Trp Thr Ala Ser Asn Tyr Asp Ser Lys Pro Trp Ile Gln Val Asn
            690                 695                 700

Leu Leu Arg Lys Met Arg Val Ser Gly Val Met Thr Gln Gly Ala Ser
705                 710                 715                 720
```

```
Arg Ala Gly Arg Ala Glu Tyr Leu Lys Thr Phe Lys Val Ala Tyr Ser
                725                 730                 735
Leu Asp Gly Arg Lys Phe Glu Phe Ile Gln Asp Glu Ser Gly Gly Asp
            740                 745                 750
Lys Glu Phe Leu Gly Asn Leu Asp Asn Asn Ser Leu Lys Val Asn Met
        755                 760                 765
Phe Asn Pro Thr Leu Glu Ala Gln Tyr Ile Lys Leu Tyr Pro Val Ser
    770                 775                 780
Cys His Arg Gly Cys Thr Leu Arg Phe Glu Leu Leu Gly Cys Glu Leu
785                 790                 795                 800
His Gly Cys Ser Glu Pro Leu Gly Leu Lys Asn Asn Thr Ile Pro Asp
                805                 810                 815
Ser Gln Met Ser Ala Ser Ser Ser Tyr Lys Thr Trp Asn Leu Arg Ala
            820                 825                 830
Phe Gly Trp Tyr Pro His Leu Gly Arg Leu Asp Asn Gln Gly Lys Ile
        835                 840                 845
Asn Ala Trp Thr Ala Gln Ser Asn Ser Ala Lys Glu Trp Leu Gln Val
    850                 855                 860
Asp Leu Gly Thr Gln Arg Gln Val Thr Gly Ile Ile Thr Gln Gly Ala
865                 870                 875                 880
Arg Asp Phe Gly His Ile Gln Tyr Val Ala Ser Tyr Lys Val Ala His
                885                 890                 895
Ser Asp Asp Gly Val Gln Trp Thr Val Tyr Glu Glu Gln Gly Ser Ser
            900                 905                 910
Lys Val Phe Gln Gly Asn Leu Asp Asn Asn Ser His Lys Lys Asn Ile
        915                 920                 925
Phe Glu Lys Pro Phe Met Ala Arg Tyr Val Arg Val Leu Pro Val Ser
    930                 935                 940
Trp His Asn Arg Ile Thr Leu Arg Leu Glu Leu Leu Gly Cys
945                 950                 955

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 13

Asn Leu Arg Val Val Arg Gly Thr Gln Val Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 14

Asp Lys Leu Cys His Met Asp Thr Ile Asp Trp Arg Asp Ile Val
1               5                   10                  15

<210> SEQ ID NO 15
<211> LENGTH: 7
<212> TYPE: PRT
<213> ORGANISM: Artificial Sequence
```

```
<220> FEATURE:
<223> OTHER INFORMATION: Synthetic peptide derived from HER3 protein
      sequence

<400> SEQUENCE: 15

Pro Cys His Glu Val Cys Lys
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 16

Ile Cys Ala Pro Gln Cys Asn Gly His Cys Phe Gly Pro Asn Pro
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 17

Asn Gly Asp Pro Trp His Lys
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 18

Asp Pro Leu Cys Ser Ser Gly Gly Cys Trp Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 19

Cys Pro His Gly Val Leu Gly Ala Lys Gly Pro
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 20

Ile Ala Gly Leu Val Val Ile Phe Met Met Leu Gly Gly Thr Phe
1               5                   10                  15
```

```
<210> SEQ ID NO 21
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 21

Leu Glu Arg Gly Glu Ser Ile Glu Pro Leu Asp
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 22

Gln Leu Leu Tyr Ser Glu Ala Lys Thr Pro Ile
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 23

Glu Ser Ile His Phe Gly Lys Tyr Thr His Gln Ser Asp Val Trp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 24

Val Trp Glu Leu Met Thr Phe Gly Ala Glu Pro Tyr Ala Gly Leu
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 25

Glu Ser Gly Pro Gly Ile Ala Pro
1               5

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence
```

<400> SEQUENCE: 26

Thr Leu Asn Arg Pro Arg Gly Ser Gln Ser Leu Leu Ser Pro Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 27

Glu Ala Glu Leu Gln Glu Lys Val Ser Met Cys Arg Ser Arg Ser
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 28

Glu Glu Asp Val Asn Gly Tyr Val Met Pro Asp
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 29

Met Pro Thr Ala Gly Thr Thr
1               5

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 30

Asp Gly Gly Gly Pro Gly Gly Asp Tyr Ala Ala Met
1               5                   10

<210> SEQ ID NO 31
<211> LENGTH: 3720
<212> TYPE: DNA
<213> ORGANISM: Homo sapiens
<220> FEATURE:
<221> NAME/KEY: misc_feature
<222> LOCATION: (1)..(3720)
<223> OTHER INFORMATION: Homo sapiens HER2 polynucleotide

<400> SEQUENCE: 31
atggagctgg cggccttgtg ccgctggggg ctcctcctcg ccctcttgcc ccccggagcc    60
gcgagcaccc aagtgtgcac cggcacagac atgaagctgc ggctccctgc cagtcccgag    120
acccacctgg acatgctccg ccacctctac cagggctgcc aggtggtgca gggaaacctg    180

```
gaactcacct acctgcccac caatgccagc ctgtccttcc tgcaggatat ccaggaggtg      240
cagggctacg tgctcatcgc tcacaaccaa gtgaggcagg tcccactgca gaggctgcgg      300
attgtgcgag gcacccagct cttTgaggac aactatgccc tggccgtgct agacaatgga      360
gacccgctga acaataccac ccctgtcaca ggggcctccc caggaggcct gcgggagctg      420
cagcttcgaa gcctcacaga gatcttgaaa ggaggggtct tgatccagcg gaaccccag      480 ctctgctacc aggacacgat tttgtggaag gacatcttcc acaagaacaa ccagctggct      540
ctcacactga tagacaccaa ccgctctcgg gcctgccacc cctgttctcc gatgtgtaag      600
ggctcccgct gctggggaga gagttctgag gattgtcaga gcctgacgcg cactgtctgt      660
gccggtggct gtgcccgctg caaggggcca ctgcccactg actgctgcca tgagcagtgt      720
gctgccggct gcacgggccc caagcactct gactgcctgg cctgcctcca cttcaaccac      780
agtggcatct gtgagctgca ctgcccagcc ctggtcacct acaacacaga cacgtttgag      840
tccatgccca tcccgaggg ccggtataca ttcggcgcca gctgtgtgac tgcctgtccc      900
tacaactacc tttctacgga cgtgggatcc tgcaccctcg tctgcccct gcacaaccaa      960 gaggtgacag cagaggatgg aacacagcgg tgtgagaagt gcagcaagcc ctgtgcccga      1020
gtgtgctatg gtctgggcat ggagcacttg cgagaggtga gggcagttac cagtgccaat      1080
atccaggagt tgctggctg caagaagatc tttgggagcc tggcattTct gccggagagc      1140
tttgatgggg acccagcctc caacactgcc ccgctccagc cagagcagct ccaagtgttt      1200
gagactctgg aagagatcac aggttaccta tacatctcag catggccgga cagcctgcct      1260
gacctcagcg tcttccagaa cctgcaagta atccggggac gaattctgca caatggcgcc      1320
tactcgctga ccctgcaagg gctgggcatc agctggctgg gctgcgctc actgagggaa      1380 ctgggcagtg gactggccct catccaccat aacacccacc tctgcttcgt gcacacggtg      1440
ccctgggacc agctctttcg gaacccgcac caagctctgc tccacactgc caaccggcca      1500
gaggacgagt gtgtgggcga gggcctggcc tgccaccagc tgtgcgcccg agggcactgc      1560
tggggtccag ggcccaccca gtgtgtcaac tgcagccagt tccttcgggg ccaggagtgc      1620
gtggaggaat gccgagtact gcaggggctc cccaggggat atgtgaatgc caggcactgt      1680
ttgccgtgcc accctgagtg tcagccccag aatggctcag tgacctgttt tggaccggag      1740
gctgaccagt gtgtggcctg tgcccactat aaggaccctc ccttctgcgt ggcccgctgc      1800
cccagcggtg tgaaacctga cctctcctac atgcccatct ggaagtttcc agatgaggag      1860
ggcgcatgcc agccttgccc catcaactgc acccactccc ctctgacgtc atcgtctct      1920 gcggtggttg gcattctgct ggtcgtggtc ttggggtgg tctttgggat cctcatcaag      1980
cgacggcagc agaagatccg gaagtacacg atgcggagac tgctgcagga aacgagctg      2040 gtggagccgc tgacacctag cggagcgatg cccaaccagg cgcagatgcg gatcctgaaa      2100
gagacggagc tgaggaaggt gaaggtgctt ggatctggcg cttttggcac agtctacaag      2160
ggcatctgga tccctgatgg ggagaatgtg aaaattccag tggccatcaa agtgttgagg      2220
gaaaacacat cccccaaagc caacaaagaa atcttagacg aagcatacgt gatggctggt      2280
gtgggctccc catatgtctc ccgccttctg gggatctgcc tgacatccac ggtgcagctg      2340
gtgacacagc ttatgcccta tggctgcctc ttagaccatg tccgggaaaa ccgcggacgc      2400
ctgggctccc aggacctgct gaactggtgt atgcagattg ccaaggggat gagctacctg      2460
gaggatgtgc ggctcgtaca cagggacttg gccgctcgga acgtgctggt caagagtccc      2520
aaccatgtca aaattacaga cttcgggctg gctcggctgc tggacattga cgagacagag      2580
```

```
taccatgcag atgggggcaa ggtgcccatc aagtggatgg cgctggagtc cattctccgc    2640
cggcggttca cccaccagag tgatgtgtgg agttatggtg tgactgtgtg ggagctgatg    2700
acttttgggg ccaaacctta cgatgggatc ccagcccggg agatccctga cctgctggaa    2760 aaggggagc ggctgcccca gcccccatc tgcaccattg atgtctacat gatcatggtc     2820
aaatgttgga tgattgactc tgaatgtcgg ccaagattcc gggagttggt gtctgaattc    2880
tcccgcatgg ccagggaccc ccagcgcttt gtggtcatcc agaatgagga cttgggccca    2940
gccagtccct tggacagcac cttctaccgc tcactgctgg aggacgatga catggggac    3000 ctggtggatg ctgaggagta tctggtaccc cagcagggct tcttctgtcc agaccctgcc    3060
ccgggcgctg ggggcatggt ccaccacagg caccgcagct catctaccag gagtggcggt    3120
ggggacctga cactagggct ggagccctct gaagaggagg cccccaggtc tccactggca    3180
ccctccgaag gggctggctc cgatgtattt gatggtgacc tgggaatggg ggcagccaag    3240
gggctgcaaa gcctccccac acatgacccc agccctctac agcggtacag tgaggacccc    3300
acagtacccc tgccctctga gactgatggc tacgttgccc ccctgacctg cagccccag    3360 cctgaatatg tgaaccagcc agatgttcgg cccagcccc cttcgccccg agagggccct     3420
ctgcctgctg cccgacctgc tggtgccact ctggaaaggg ccaagactct ctccccaggg   3480
aagaatgggg tcgtcaaaga cgtttttgcc tttgggggtg ccgtggagaa ccccgagtac   3540
ttgacacccc agggaggagc tgcccctcag ccccacccctc ctcctgcctt cagcccagcc   3600
ttcgacaacc tctattactg ggaccaggac ccaccagagc gggggctcc acccagcacc    3660 ttcaaaggga cacctacggc agagaaccca gagtacctgg gtctggacgt gccagtgtga   3720

<210> SEQ ID NO 32
<211> LENGTH: 335
<212> TYPE: DNA
<213> ORGANISM: Homo sapiens
<220> FEATURE:
<221> NAME/KEY: misc_feature
<222> LOCATION: (1)..(335)
<223> OTHER INFORMATION: Homo sapiens HER2 polynucleotide

<400> SEQUENCE: 32
atggagctgg cggccttgtg ccgctggggg ctcctcctcg ccctcttgcc ccccggagcc    60
gcgagcaccc aagtgtgcac cggcacagac atgaagctgc ggctccctgc cagtcccgag   120
acccacctgg acatgctccg ccacctctac caggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aacta                               335

<210> SEQ ID NO 33
<211> LENGTH: 3720
<212> TYPE: DNA
<213> ORGANISM: Homo sapiens
<220> FEATURE:
<221> NAME/KEY: misc_feature
<222> LOCATION: (1)..(3720)
<223> OTHER INFORMATION: Homo sapiens HER2 polynucleotide

<400> SEQUENCE: 33
atggagctgg cggccttgtg ccgctggggg ctcctcctcg ccctcttgcc ccccggagcc    60
gcgagcaccc aagtgtgcac cggcacagac atgaagctgc ggctccctgc cagtcccgag   120
```

-continued

```
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acaataccac ccctgtcaca ggggcctccc caggaggcct gcgggagctg     420
cagcttcgaa gcctcacaga gatcttgaaa ggagggtct tgatccagcg gaaccccag      480
ctctgctacc aggacacgat tttgtggaag acatcttcc acaagaacaa ccagctggct     540
ctcacactga tagacaccaa ccgctctcgg gcctgccacc cctgttctcc gatgtgtaag    600
ggctcccgct gctggggaga gagttctgag gattgtcaga gctgacgcg cactgtctgt     660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgcccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg gctgcgctc actgagggaa    1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccaggagt atgtgaatgc caggcactgt    1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactccc ctctgacgtc catcgtctct   1920
gcggtggttg gcattctgct ggtcgtggtc ttggggtgg tctttgggat cctcatcaag   1980
cgacggcagc agaagatccg gaagtagacg atgcggagac tgctgcagga aacggagctg   2040
gtggagccgc tgacacctag cggagcgatg cccaaccagg cgcagatgcg gatcctgaaa    2100
gagacggagc tgaggaaggt gaaggtgctt ggatctggcg cttttggcac agtctacaag   2160
ggcatctgga tccctgatgg ggagaatgtg aaaattccag tggccatcaa agtgttgagg   2220
gaaaacacat cccccaaagc caacaaagaa atcttagacg aagcatacgt gatggctggt   2280
gtgggctccc catatgtctc ccgccttctg gggatctgcc tgacatccac ggtgcagctg   2340
gtgacacagc ttatgcccta tggctgcctc ttagaccatg tccgggaaaa ccgcggacgc   2400
ctgggctccc aggacctgct gaactggtgt atgcagattg ccaaggggat gagctacctg   2460
gaggatgtgc ggctcgtaca cagggacttg gccgctcgga acgtgctggt caagagtccc   2520
```

-continued

```
aaccatgtca aaattacaga cttcgggctg gctcggctgc tggacattga cgagacagag    2580
taccatgcag atgggggcaa ggtgcccatc aagtggatgg cgctggagtc cattctccgc    2640
cggcggttca cccaccagag tgatgtgtgg agttatggtg tgactgtgtg ggagctgatg    2700
acttttgggg ccaaaccttcc cgatgggatc ccagcccggg agatccctga cctgctggaa    2760
```
(Note: the row above corresponds to: acttttgggg ccaaaccttta cgatgggatc ccagcccggg agatccctga cctgctggaa 2760)

```
aaggggagc ggctgcccca gcccccatc tgcaccattg atgtctacat gatcatggtc      2820
aaatgttgga tgattgactc tgaatgtcgg ccaagattcc gggagttggt gtctgaattc     2880
tcccgcatgg ccagggaccc ccagcgcttt gtggtcatcc agaatgagga cttgggccca    2940
gccagtccct tggacagcac cttctaccgc tcactgctgg aggacgatga catgggggac    3000
ctggtggatg ctgaggagta tctggtaccc cagcagggct tcttctgtcc agaccctgcc    3060
ccgggcgctg ggggcatggt ccaccacagg caccgcagct catctaccag gagtggcggt    3120
ggggacctga cactagggct ggagccctct gaagaggagg cccccaggtc tccactggca    3180
ccctccgaag gggctggctc cgatgtattt gatggtgacc tgggaatggg ggcagccaag    3240
gggctgcaaa gcctccccac acatgacccc agccctctac agcggtacag tgaggacccc    3300
acagtacccc tgccctctga gactgatggc tacgttgccc ccctgacctg cagccccag     3360
```
(Note: previous row reads: acagtacccc tgccctctga gactgatggc tacgttgccc ccctgacctg cagccccag 3360)

```
cctgaatatg tgaaccagcc agatgttcgg ccccagcccc cttcgccccg agagggccct    3420
ctgcctgctg cccgacctgc tggtgccact ctggaaaggg ccaagactct ctccccaggg    3480
aagaatgggg tcgtcaaaga cgtttttgcc tttgggggtg ccgtggagaa ccccgagtac    3540
ttgacacccc aggaggagc tgcccctcag ccccaccctc ctcctgcctt cagcccagcc     3600
```
(Row reads: ttgacacccc aggaggagagc tgcccctcag ccccaccctc ctcctgcctt cagcccagcc 3600)

```
ttcgacaacc tctattactg ggaccaggac ccaccagagc gggggggctcc acccagcacc    3660 ttcaaaggga cacctacggc agagaaccca gagtacctgg gtctggacgt gccagtgtga    3720
```

<210> SEQ ID NO 34
<211> LENGTH: 331
<212> TYPE: PRT
<213> ORGANISM: Homo sapiens
<220> FEATURE:
<221> NAME/KEY: misc_feature
<222> LOCATION: (1)..(331)
<223> OTHER INFORMATION: Homo sapiens HER2 polypeptide

<400> SEQUENCE: 34

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 35
<211> LENGTH: 1342
<212> TYPE: PRT
<213> ORGANISM: Homo sapiens
<220> FEATURE:
<221> NAME/KEY: misc_feature
<222> LOCATION: (1)..(1342)
<223> OTHER INFORMATION: Homo sapiens HER2 polypeptide

<400> SEQUENCE: 35

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Gly Val Tyr Ile Glu Lys Asn Asp Lys Leu Cys His Met Asp Thr
145                 150                 155                 160

```
Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
```

-continued

```
            580                 585                 590
Val Leu Gly Ala Lys Gly Pro Ile Tyr Lys Tyr Pro Asp Val Gln Asn
            595                 600                 605
Glu Cys Arg Pro Cys His Glu Asn Cys Thr Gln Gly Cys Lys Gly Pro
            610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                    645                 650                 655
Met Met Leu Gly Gly Thr Phe Leu Tyr Trp Arg Gly Arg Arg Ile Gln
                    660                 665                 670
Asn Lys Arg Ala Met Arg Arg Tyr Leu Glu Arg Gly Glu Ser Ile Glu
                    675                 680                 685
Pro Leu Asp Pro Ser Glu Lys Ala Asn Lys Val Leu Ala Arg Ile Phe
                    690                 695                 700
Lys Glu Thr Glu Leu Arg Lys Leu Lys Val Leu Gly Ser Gly Val Phe
705                 710                 715                 720
Gly Thr Val His Lys Gly Val Trp Ile Pro Glu Gly Glu Ser Ile Lys
                    725                 730                 735
Ile Pro Val Cys Ile Lys Val Ile Glu Asp Lys Ser Gly Arg Gln Ser
                    740                 745                 750
Phe Gln Ala Val Thr Asp His Met Leu Ala Ile Gly Ser Leu Asp His
                    755                 760                 765
Ala His Ile Val Arg Leu Leu Gly Leu Cys Pro Gly Ser Ser Leu Gln
                    770                 775                 780
Leu Val Thr Gln Tyr Leu Pro Leu Gly Ser Leu Leu Asp His Val Arg
785                 790                 795                 800
Gln His Arg Gly Ala Leu Gly Pro Gln Leu Leu Leu Asn Trp Gly Val
                    805                 810                 815
Gln Ile Ala Lys Gly Met Tyr Tyr Leu Glu Glu His Gly Met Val His
                    820                 825                 830
Arg Asn Leu Ala Ala Arg Asn Val Leu Leu Lys Ser Pro Ser Gln Val
                    835                 840                 845
Gln Val Ala Asp Phe Gly Val Ala Asp Leu Leu Pro Pro Asp Asp Lys
                    850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                    885                 890                 895
Tyr Gly Val Thr Val Trp Glu Leu Met Thr Phe Gly Ala Glu Pro Tyr
                    900                 905                 910
Ala Gly Leu Arg Leu Ala Glu Val Pro Asp Leu Leu Glu Lys Gly Glu
                    915                 920                 925
Arg Leu Ala Gln Pro Gln Ile Cys Thr Ile Asp Val Tyr Met Val Met
                    930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                    965                 970                 975
Val Ile Lys Arg Glu Ser Gly Pro Gly Ile Ala Pro Gly Pro Glu Pro
                    980                 985                 990
His Gly Leu Thr Asn Lys Lys Leu  Glu Glu Val Glu Leu  Glu Pro Glu
                    995                 1000                1005
```

Leu Asp Leu Asp Leu Asp Leu Glu Ala Glu Glu Asp Asn Leu Ala
    1010                1015                1020

Thr Thr Thr Leu Gly Ser Ala Leu Ser Leu Pro Val Gly Thr Leu
    1025                1030                1035

Asn Arg Pro Arg Gly Ser Gln Ser Leu Leu Ser Pro Ser Ser Gly
    1040                1045                1050

Tyr Met Pro Met Asn Gln Gly Asn Leu Gly Gly Ser Cys Gln Glu
    1055                1060                1065

Ser Ala Val Ser Gly Ser Ser Glu Arg Cys Pro Arg Pro Val Ser
    1070                1075                1080

Leu His Pro Met Pro Arg Gly Cys Leu Ala Ser Glu Ser Ser Glu
    1085                1090                1095

Gly His Val Thr Gly Ser Glu Ala Glu Leu Gln Glu Lys Val Ser
    1100                1105                1110

Met Cys Arg Ser Arg Ser Arg Ser Arg Ser Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Glu Tyr Glu Tyr Met Asn Arg Arg
    1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 36
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens HER2 polypeptide

<400> SEQUENCE: 36

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
```

```
                        405                 410                 415
Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Asn Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 37
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens HER2 polypeptide

<400> SEQUENCE: 37

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160
```

```
Gly Arg Glu Arg Leu Ala Ser Thr Asn Asp Lys Gly Ser Met Ala Met
            165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
            245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
            325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
            405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
            485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Ser Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
            565                 570                 575
```

His Ser Leu Gln Lys Tyr Tyr Ile Thr Gly Glu Ala Glu Gly Phe Pro
            580                 585                 590
Ala Thr Val
        595

<210> SEQ ID NO 38
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens HER polypeptide

<400> SEQUENCE: 38

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro

```
                    325                 330                 335
        Phe Ser Glu Ala Ser Met Met Gly Leu Leu Thr Asn Leu Ala Asp Arg
                340                 345                 350
        Glu Leu Val His Met Ile Asn Trp Ala Lys Arg Val Pro Gly Phe Val
                355                 360                 365
        Asp Leu Thr Leu His Asp Gln Val His Leu Leu Glu Cys Ala Trp Leu
                370                 375                 380
        Glu Ile Leu Met Ile Gly Leu Val Trp Arg Ser Met Glu His Pro Gly
        385                 390                 395                 400
        Lys Leu Leu Phe Ala Pro Asn Leu Leu Leu Asp Arg Asn Gln Gly Lys
                        405                 410                 415
        Cys Val Glu Gly Met Val Glu Ile Phe Asp Met Leu Leu Ala Thr Ser
                        420                 425                 430
        Ser Arg Phe Arg Met Met Asn Leu Gln Gly Glu Glu Phe Val Cys Leu
                        435                 440                 445
        Lys Ser Ile Ile Leu Leu Asn Ser Gly Val Tyr Thr Phe Leu Ser Ser
                        450                 455                 460
        Thr Leu Lys Ser Leu Glu Glu Lys Asp His Ile His Arg Val Leu Asp
        465                 470                 475                 480
        Lys Ile Thr Asp Thr Leu Ile His Leu Met Ala Lys Ala Gly Leu Thr
                        485                 490                 495
        Leu Gln Gln Gln His Gln Arg Leu Ala Gln Leu Leu Leu Ile Leu Ser
                        500                 505                 510
        His Ile Arg His Met Ser Asn Lys Gly Met Glu His Leu Tyr Ser Met
                        515                 520                 525
        Lys Cys Lys Asn Val Val Pro Leu Tyr Gly Leu Leu Leu Glu Met Leu
                        530                 535                 540
        Asp Ala His Arg Leu His Ala Pro Thr Ser Arg Gly Gly Ala Ser Val
        545                 550                 555                 560
        Glu Glu Thr Asp Gln Ser His Leu Ala Thr Ala Gly Ser Thr Ser Ser
                        565                 570                 575
        His Ser Leu Gln Lys Tyr Tyr Ile Thr Gly Glu Ala Glu Gly Phe Pro
                        580                 585                 590
        Ala Thr Val
                595

<210> SEQ ID NO 39
<211> LENGTH: 595
<212> TYPE: PRT
<213> ORGANISM: Homo sapiens
<220> FEATURE:
<221> NAME/KEY: misc_feature
<222> LOCATION: (1)..(595)
<223> OTHER INFORMATION: Homo sapiens HER2 polypeptide

<400> SEQUENCE: 39

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80
```

```
Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Arg Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495
```

```
Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 40
<211> LENGTH: 1239
<212> TYPE: PRT
<213> ORGANISM: Homo sapiens
<220> FEATURE:
<221> NAME/KEY: misc_feature
<222> LOCATION: (1)..(1239)
<223> OTHER INFORMATION: Homo sapiens ESR1 polypeptide

<400> SEQUENCE: 40

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240
```

```
Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Val Ser
625                 630                 635                 640

Ala Val Val Gly Ile Leu Leu Val Val Val Leu Gly Val Val Phe Gly
                645                 650                 655
```

-continued

```
Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
        675                 680                 685

Ala Met Pro Asn Gln Ala Gln Met Arg Ile Leu Lys Glu Thr Glu Leu
    690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
                725                 730                 735

Lys Val Leu Arg Glu Asn Thr Ser Pro Lys Ala Asn Lys Glu Ile Leu
            740                 745                 750

Asp Glu Ala Tyr Val Met Ala Gly Val Gly Ser Pro Tyr Val Ser Arg
        755                 760                 765

Leu Leu Gly Ile Cys Leu Thr Ser Thr Val Gln Leu Val Thr Gln Leu
    770                 775                 780

Met Pro Tyr Gly Cys Leu Leu Asp His Val Arg Glu Asn Arg Gly Arg
785                 790                 795                 800

Leu Gly Ser Gln Asp Leu Leu Asn Trp Cys Met Gln Ile Ala Lys Gly
                805                 810                 815

Met Ser Tyr Leu Glu Asp Val Arg Leu Val His Arg Asp Leu Ala Ala
            820                 825                 830

Arg Asn Val Leu Val Lys Ser Pro Asn His Val Lys Ile Thr Asp Phe
        835                 840                 845

Gly Leu Ala Arg Leu Leu Asp Ile Asp Glu Thr Glu Tyr His Ala Asp
    850                 855                 860

Gly Gly Lys Val Pro Ile Lys Trp Met Ala Leu Glu Ser Ile Leu Arg
865                 870                 875                 880

Arg Arg Phe Thr His Gln Ser Asp Val Trp Ser Tyr Gly Val Thr Val
                885                 890                 895

Trp Glu Leu Met Thr Phe Gly Ala Lys Pro Tyr Asp Gly Ile Pro Ala
            900                 905                 910

Arg Glu Ile Pro Asp Leu Leu Glu Lys Gly Glu Arg Leu Pro Gln Pro
        915                 920                 925

Pro Ile Cys Thr Ile Asp Val Tyr Met Ile Met Val Lys Cys Trp Met
    930                 935                 940

Ile Asp Ser Glu Cys Arg Pro Arg Phe Arg Glu Leu Val Ser Glu Phe
945                 950                 955                 960

Ser Arg Met Ala Arg Asp Pro Gln Arg Phe Val Val Ile Gln Asn Glu
                965                 970                 975

Asp Leu Gly Pro Ala Ser Pro Leu Asp Ser Thr Phe Tyr Arg Ser Leu
            980                 985                 990

Leu Glu Asp Asp Asp Met Gly Asp Leu Val Asp Ala Glu Glu Tyr Leu
        995                 1000                1005

Val Pro Gln Gln Gly Phe Phe Cys Pro Asp Pro Ala Pro Gly Ala
    1010                1015                1020

Gly Gly Met Val His His Arg His Arg Ser Ser Ser Thr Arg Ser
    1025                1030                1035

Gly Gly Gly Asp Leu Thr Leu Gly Leu Glu Pro Ser Glu Glu Glu
    1040                1045                1050

Ala Pro Arg Ser Pro Leu Ala Pro Ser Glu Gly Ala Gly Ser Asp
    1055                1060                1065
```

```
Val Phe Asp Gly Asp Leu Gly Met Gly Ala Ala Lys Gly Leu Gln
1070                1075                1080

Ser Leu Pro Thr His Asp Pro Ser Pro Leu Gln Arg Tyr Ser Glu
1085                1090                1095

Asp Pro Thr Val Pro Leu Pro Ser Glu Thr Asp Gly Tyr Val Ala
1100                1105                1110

Pro Leu Thr Cys Ser Pro Gln Pro Glu Tyr Val Asn Gln Pro Asp
1115                1120                1125

Val Arg Pro Gln Pro Pro Ser Pro Arg Glu Gly Pro Leu Pro Ala
1130                1135                1140

Ala Arg Pro Ala Gly Ala Thr Leu Glu Arg Ala Lys Thr Leu Ser
1145                1150                1155

Pro Gly Lys Asn Gly Val Val Lys Asp Val Phe Ala Phe Gly Gly
1160                1165                1170

Ala Val Glu Asn Pro Glu Tyr Leu Thr Pro Gln Gly Gly Ala Ala
1175                1180                1185

Pro Gln Pro His Pro Pro Pro Ala Phe Ser Pro Ala Phe Asp Asn
1190                1195                1200

Leu Tyr Tyr Trp Asp Gln Asp Pro Pro Glu Arg Gly Ala Pro Pro
1205                1210                1215

Ser Thr Phe Lys Gly Thr Pro Thr Ala Glu Asn Pro Glu Tyr Leu
1220                1225                1230

Gly Leu Asp Val Pro Val
1235

<210> SEQ ID NO 41
<211> LENGTH: 111
<212> TYPE: PRT
<213> ORGANISM: Homo sapiens
<220> FEATURE:
<221> NAME/KEY: misc_feature
<222> LOCATION: (1)..(111)
<223> OTHER INFORMATION: Homo sapiens ESR1 polypeptide

<400> SEQUENCE: 41

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn
            100                 105                 110

<210> SEQ ID NO 42
<211> LENGTH: 668
<212> TYPE: PRT
<213> ORGANISM: Homo sapiens
<220> FEATURE:
<221> NAME/KEY: misc_feature
<222> LOCATION: (1)..(668)
<223> OTHER INFORMATION: Homo sapiens ESR1 polypeptide
```

<400> SEQUENCE: 42

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415
```

```
Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Val Ser
625                 630                 635                 640

Ala Val Val Gly Ile Leu Leu Val Val Val Leu Gly Val Val Phe Gly
                645                 650                 655

Ile Leu Ile Lys Arg Arg Gln Gln Lys Ile Arg Lys
            660                 665

<210> SEQ ID NO 43
<211> LENGTH: 331
<212> TYPE: PRT
<213> ORGANISM: Homo sapiens
<220> FEATURE:
<221> NAME/KEY: misc_feature
<222> LOCATION: (1)..(331)
<223> OTHER INFORMATION: Homo sapiens ESR1 polypeptide

<400> SEQUENCE: 43

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95
```

```
Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
        130                 135                 140

Gly Gly Val Tyr Ile Glu Lys Asn Asp Lys Leu Cys His Met Asp Thr
145                 150                 155                 160

Ile Asp Trp Arg Asp Ile Val Arg Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 44
<211> LENGTH: 1342
<212> TYPE: PRT
<213> ORGANISM: Homo sapiens
<220> FEATURE:
<221> NAME/KEY: misc_feature
<222> LOCATION: (1)..(1342)
<223> OTHER INFORMATION: Homo sapiens ESR1 polypeptide

<400> SEQUENCE: 44

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110
```

```
Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
        130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525
```

```
Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
930                 935                 940
```

```
Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
                980                 985                 990

His Gly Leu Thr Asn Lys Lys Leu  Glu Glu Val Glu Leu  Glu Pro Glu
            995             1000                 1005

Leu Asp  Leu Asp  Leu Asp  Leu  Glu Ala Glu Glu Asp  Asn Leu Ala
    1010              1015                 1020

Thr Thr  Thr Leu Gly Ser Ala  Leu Ser Leu Pro Val  Gly Thr Leu
    1025                 1030                 1035

Asn Arg  Pro Arg Gly Ser Gln  Ser Leu Leu Ser Pro  Ser Ser Gly
    1040                 1045                 1050

Tyr Met  Pro Met Asn Gln Gly  Asn Leu Gly Gly Ser  Cys Gln Glu
    1055                 1060                 1065

Ser Ala  Val Ser Gly Ser Ser  Glu Arg Cys Pro Arg  Pro Val Ser
    1070                 1075                 1080

Leu His  Pro Met Pro Arg Gly  Cys Leu Ala Ser Glu  Ser Ser Glu
    1085                 1090                 1095

Gly His  Val Thr Gly Ser Glu  Ala Glu Leu Gln Glu  Lys Val Ser
    1100                 1105                 1110

Met Cys  Arg Ser Arg Ser Arg  Ser Arg Ser Pro Arg  Pro Arg Gly
    1115                 1120                 1125

Asp Ser  Ala Tyr His Ser Gln  Arg His Ser Leu Leu  Thr Pro Val
    1130                 1135                 1140

Thr Pro  Leu Ser Pro Pro Gly  Leu Glu Glu Glu Asp  Val Asn Gly
    1145                 1150                 1155

Tyr Val  Met Pro Asp Thr His  Leu Lys Gly Thr Pro  Ser Ser Arg
    1160                 1165                 1170

Glu Gly  Thr Leu Ser Ser Val  Gly Leu Ser Ser Val  Leu Gly Thr
    1175                 1180                 1185

Glu Glu  Glu Asp Glu Asp Glu  Glu Tyr Glu Tyr Met  Asn Arg Arg
    1190                 1195                 1200

Arg Arg  His Ser Pro Pro His  Pro Pro Arg Pro Ser  Ser Leu Glu
    1205                 1210                 1215

Glu Leu  Gly Tyr Glu Tyr Met  Asp Val Gly Ser Asp  Leu Ser Ala
    1220                 1225                 1230

Ser Leu  Gly Ser Thr Gln Ser  Cys Pro Leu His Pro  Val Pro Ile
    1235                 1240                 1245

Met Pro  Thr Ala Gly Thr Thr  Pro Asp Glu Asp Tyr  Glu Tyr Met
    1250                 1255                 1260

Asn Arg  Gln Arg Asp Gly Gly  Gly Pro Gly Gly Asp  Tyr Ala Ala
    1265                 1270                 1275

Met Gly  Ala Cys Pro Ala Ser  Glu Gln Gly Tyr Glu  Glu Met Arg
    1280                 1285                 1290

Ala Phe  Gln Gly Pro Gly His  Gln Ala Pro His Val  His Tyr Ala
    1295                 1300                 1305

Arg Leu  Lys Thr Leu Arg Ser  Leu Glu Ala Thr Asp  Ser Ala Phe
    1310                 1315                 1320
```

-continued

```
Asp Asn Pro Asp Tyr Trp His  Ser Arg Leu Phe Pro  Lys Ala Asn
    1325                1330             1335

Ala Gln Arg Thr
    1340
```